US006713043B2

(12) United States Patent
Kabbash et al.

(10) Patent No.: US 6,713,043 B2

(45) **Date of Patent: *Mar. 30, 2004**

(54) ANTIMICROBIAL ACTIVITY OF GEMFIBROZIL

(75) Inventors: Christina Kabbash, Greenwich, CT (US); Howard A. Shuman, Larchmont, NY (US); Samuel C. Silverstein, New York, NY (US); Phyllis Della-Latta, Brooklyn, NY (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/608,712

(22) Filed: Feb. 29, 1996

(65) Prior Publication Data

US 2003/0100042 A1 May 29, 2003

(51) Int. Cl.[7] ........................ A61K 51/00; A61M 36/14

(52) U.S. Cl. ...................... 424/1.69; 424/1.11; 424/9.1; 424/1.65; 435/25

(58) Field of Search ................................ 435/4, 29, 32, 435/183, 25; 544/1; 424/1.11, 1.65, 1.69, 9.1

(56) References Cited

U.S. PATENT DOCUMENTS

| | | | | |
|---|---|---|---|---|
| 3,674,836 A | * | 7/1972 | Creger | 206/473 |
| 4,859,703 A | | 8/1989 | Krause | |
| 4,891,220 A | | 1/1990 | Donzis | |
| 5,422,372 A | | 6/1995 | Silverstein et al. | |
| 5,837,480 A | | 11/1998 | Sacchettini et al. | |
| 6,531,291 B1 | * | 3/2003 | Kabbash et al. | 435/25 |

FOREIGN PATENT DOCUMENTS

WO WO9937800 7/1999

OTHER PUBLICATIONS

Vernon et al, Biochimica et Biophysica Acta, 788, 124–131 'The Presence' of Essential Arginine Residues at the NADPH Binding Sites of B–Ketoacyl Reductose and Enyl Reductose Domains of the Multi–functional Fatty Acid Synthetase of Chicken Liver, 1984.*

Hashimoto et al (Apr. 1997), Bid. Pharm. Bull., vol. 20, No. 4, pp. 315–321, Effect of Gemfibrozil on Centrifugal Behavior of Rat Peroxisomes and Activities of Perokisomal Enzymes Involved in Lipio Metabolism.*

Baldock et al (1996, Dec.) , Science, vol. 274, pp. 2107–2110, "A Mechanism of Drug, Action Revealed by Structural Studies of Enolyl Reductase".*

The Merck Index, 10th ed., Merck & Co., Inc. Rahway, N.J., 1983, #4246.

C. Kabbash, H. Shuman, S. Silverstein, P. Della–Latta, J. Blanchard, U.S. Serial No. 09/438144, filed Nov. 10, 1999.

The Merck Index, $10^{th}$ Ed., Merck & Co., Inc., Rahway, New Jersey, 1983, No. 4246.

Vernon et al. (1984) The Presence of Essential Arginine Residues at the NADPH–Binding Sites of β–Ketoacyl Reductase, And Enoyl Reductase Domains of the Multifunctional Fatty Acid Synthetase of Chicken Liver, *Biochim. et Biophys. Acta.* vol. 788, pp. 124–131.

Clements, P.R. and Barden, R. E. (1982) Irreversible Inhibition of Fatty Acid Synthase From Rat Mammary Gland With S–(4–bromo–2,3–dioxobutyl) –CoA. *Biochem. J.* vol. 207, pp. 291–296.

(List continued on next page.)

*Primary Examiner*—Dameron L. Jones

(74) *Attorney, Agent, or Firm*—John P. White; Cooper & Dunham LLP

(57) ABSTRACT

The present invention provides for a method for inhibiting growth of a bacterium which consists essentially of contacting the bacterium with a compound having the structure:

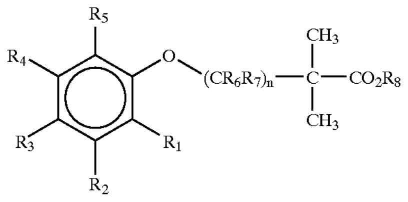

wherein each of $R_1$, $R_2$, $R_3$, $R_4$, $R_5$ and $R_6$ may be independently H, F, Cl, Br, I, —OH, —$OR_7$, —CN, —$COR_7$, —$SR_7$, —$N(R_7)_2$, —$NR_7COR_8$, —$NO_2$, —$(CH_2)_pOR_7$, —$(CH_2)_pX(R_7)_2$, —$(CH_2)_pXR_7COR_8$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl; wherein a linkage to the benzene ring may alternatively be —N—, —S—, —O— or —C—; wherein $R_7$ or $R_8$ may be independently H, F, Cl, Br, I, —OH, —CN, —COH, —$SH_2$, —$NH_2$, —NHCOH, —$(CH_2)_pOH$, —$(CH_2)_pX(CH_2)$, —$(CH_2)_pXCOH$, a straight chain or branched, substituted or unsubstituted $C_1$–$C_{10}$ alkyl, thioalkyl, methylene thioalkyl, acyl, phenyl, substituted phenyl, or heteroaryl; wherein A may be —$N_2$—, —NH—, —C=C=$CH_2$—, —C≡C—$C_2HOH$—, —C≡C—$CH_2$—, —$CH_2$—$CH_2$—O—, —$CH_2$—$CH_2$—$CH_2$—O—, —S—, —S(=O)$_2$—, —C=O—, —C=O—O—, —NH—C=O—, —C=O—NH—.

17 Claims, 24 Drawing Sheets

OTHER PUBLICATIONS

Bergler, H. et al. (1996) The enoyl–[acyl–carrier–protein] reductase (FabI) of *Escherichia coli*, which catalyzes a key regulatory step in fatty acid biosynthesis, accepts NADH and NADPH as cofactors and is inhibited by palmitoyl–CoA. *Eur. J. Biochem.* vol. 242, pp. 689–694.

Heath, R. J. and Rock, C. O. (1996) Regulation of Fatty Acid Elongation and Initiation by Acyl–Acyl Carrier Protein in *Escherichia coli. J. Biol. Chem.* vol 271, No. 4, pp. 1833–1836.

Cardon, J. W. and Hammes, G. G. (1983) Kinetic and Structural Investigation of Acyl–binding Sites on Avian Fatty Acid Synthase. *J. Biol. Chem.* vol. 258, No. 8, pp. 4802–4807.

Bronfman, M., et al. (1992) Hypolipidaemic drugs are activated to acyl–CoA esters in isolated rat hepatocytes. *Biochem. J.* vol. 284, pp. 289–295.

Amigo, L. et al. (1992) Subcellular distribution and characteristics of ciprofibroyl–CoA synthetase in rat liver. *Biochem. J.* vol. 284, pp. 283–287.

Urrea, R. and Bronfman, M. (1996) Species Differences in the Intracellular Distribution of Ciprofibroyl–CoA hydrolase. Implications for peroxisome proliferation. FEBS Letters vol. 389, pp. 219–223.

* cited by examiner

FIGURE 4

Sensitivity Screen

| Organism | Sensitive? |
|---|---|
| **Legionella pneumophila** | **yes** |
| | |
| Acinetobacter sp. | no |
| Actinobacillus sp. | no |
| Azobacter vinlandi | no |
| Bacillus aureus | no |
| **Bacillus subtilis** | **yes** |
| Cardiobacterium sp. | no |
| **Caulobacter crescentus** | **yes** |
| Citrobacter freundi | yes |
| (4) Corynebacterium sp. | no |
| Enterobacter cloacae | no |
| Enterococcus faecalis | no |
| Escherichia coli | no |
| Klebsiella pneumonia | no |
| Leuconostoc sp. | no |
| **(6) Nocardia sp.** | **yes** |
| Pediococcus sp. | no |
| Proteus mirabilis | no |
| Pseudomonas aeruginosa | no |
| Rhizobium nulilo | no |
| **Rhodobacter spheroides** | **yes** |
| (3) Rhodococcus sp. | no |
| Salmonella sp. | no |
| Serratia marcescens | no |
| Shigella sp. | no |
| Xanthomonas sp. | no |
| | |
| (5/6) Group A Streptococcus sp | no |
| **(1/6) Group A Streptococcus sp.** | **yes** |
| | |
| **(3) Coag neg Staphylococcus aureus** | **yes** |
| (3) Coag pos Staphylococcus aureus | no. |
| | |
| **Mycobacterium tuberculosis** | **yes** |
| Mycobacterium chelonei | no |
| Mycobacterium fortuitum | no |

FIGURE 5

MDR-*M. tuberculosis* Sensitivity to GFZ

| Strain | GFZ 0ug/ml | GFZ 25ug/ml | GFZ 50ug/ml | GFZ 100ug/ml | GFZ 200ug/ml |
|---|---|---|---|---|---|
| W54410 | ++ | + | 35 | - | - |
| 5260 | ++ | ++ | 43 | - | - |
| T30234 | ++ | ++ | + | - | - |
| O81256 | ++ | ++ | + | - | - |
| W19521 | ++ | ++ | + | - | - |
| O80154 | +++ | ++ | + | - | - |
| CDC N | ++ | ND | + | - | - |
| H52578 | ++ | ++ | ++ | - | - |
| CDC P | +++ | ND | +++ | - | - |
| O80711 | ++ | ++ | + | 6 | - |
| S 15674 | ++ | ++ | + | 10 | - |
| M23294 | ++ | ++ | ++ | 4.5 | - |
| CDC K | +++ | ND | ++ | 6 | - |
| M41151 | ++ | ++ | ++ | 7.5 | - |
| F16285 | ++ | ++ | ++ | 10 | - |
| T45777 | +++ | +++ | +++ | + | - |
| Avanto | +++ | ND | +++ | + | - |
| Harrison | +++ | ND | +++ | +- | - |
| CDC L | +++ | ND | ++++ | ++ | - |
| Montalvo | ++++ | ND | ++++ | ++ | - |
| MTB2517 | ++++ | ND | ++++ | ++ | - |

L.pnneumophilia

F4b 4.5 (-GFZ)

L.pnneumophilia

F4b 4.5 (-GFZ)

L. pneumophila
CYE plate

FIGURE 16

| | Zones of Inhibition diameter (mm) | |
|---|---|---|
| | Permissive Temperature | Restrictive Temperature |
| STRAIN | 30C | 42C |
| ts100 | 0 | no growth |
| ts100:pBSK | 0 | no growth |
| ts100:pBSK2.1 | 0 | 19 |
| 101envM+ | 0 | 0 |
| 101envM+:pBSK | 0 | 0 |
| 101envM+:pBSK2.1 | 0 | 0 |
| DH5a | 0 | 0 |
| DH5a:pBSK | 0 | 0 |
| DH5a:pBSK | 0 | 0 |

ANTIMICROBIAL ACTIVITY OF GEMFIBROZIL

The invention disclosed herein was made with Government support under Grant No. AI23549 and AI20516 from NIAID. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

Gemfibrozil (GFZ) is a compound that has been utilized as a drug for increasing intracellular accumulation of hydrophilic anionic agents (U.S. Pat. No. 5,422,372, issued Jun. 6, 1995) and as a lipid regulating composition (U.S. Pat. No. 4,859,703, issued Aug. 22, 1989). Gemfibrozil has been shown to be effective in increasing the amount of cholesterol excreted in to bile. (Ottmar Leiss et al., Metabolism, 34(1): 74–82 (1985)). Gemfibrozil is described in U.S. Pat. No. 3,674,836 and in The Merck Index, 11 ed., Merck & Co., Inc. Rahway, N.J. 1989; #4280. Gemfibrozil, a drug which therapeutically lowers triglycerides and raises HDL-cholesterol levels, previously has not been reported to have antimicrobial activity. (Brown, 1987; Oliver et al., 1978 and Palmer et al., 1978).

SUMMARY OF THE INVENTION

The present invention provides for a method for inhibiting growth of a bacterium which consists essentially of contacting the bacterium with a compound having the structure

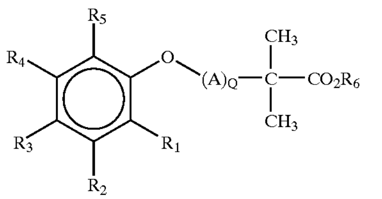

In the compound each of $R_1$,, $R_2$, $R_3$, $R_4$, $R_5$ and $R_6$ may be independently H, F, Cl, Br, I, —OH, —$OR_7$, —CN, —$COR_7$, —$SR_7$, —$N(R_7)_2$, —$NR_7COR_8$, —$NO_2$, —$(CH_2)_pOR_7$, —$(CH_2)_pX(R_7)_2$, —$(CH_2)_pXR_7COR_8$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl; wherein $R_7$ or $R_8$ may be independently H, F, Cl, Br, I, —OH, —CN, —COH, —$SH_2$, —$NH_2$, —NHCOH, —$(CH_2)_pOH$, —$(CH_2)_pX(CH_2)$, —$(CH_2)_pXCOH$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl; wherein A may be —$N_2$—, —NH—, —C=C=$CH_2$—, —C≡C—$C_2HOH$—, —C≡C—$CH_2$—, —$CH_2$—$CH_2O$—, —$CH_2$—$CH_2$—$CH_2$—O—, —S—, —S(=O)$_2$—, —C=O—, —C=O—O—, —NH—C=O—, —C=O—NH—; and wherein Q, p, n and x may independently be an integer from 1 to 10, or if Q is 1 A may be a ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and can optionally be interrupted 1 to 3 times by —O— or —S— or —N—; or a pharmaceutically acceptable salt or ester thereof, which compound is present in a concentration effective to inhibit growth of the bacterium. In this method, A may be an ($C_1$–$C_{10}$)-alkylene chain, ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and can optionally be interrupted 1 to 3 times by —O— or —S— or —N—; and wherein the ether linkage to the benzene ring may be alternatively —S—, —N— or —C—.

BRIEF DESCRIPTION OF THE FIGURES

FIG. 4. Bacteria were screened for sensitivity to gemfibrozil using a zone of inhibition assay. The assay was performed by adding bacteria to a suitable nutrient agar plate, adding a disk containing gemfibrozil to the plate, and then incubating the plate at the appropriate temperature. The presence of a zone of inhibition (area around the disk where no growth occurred) was considered positive for sensitivity.

FIG. 5. Twenty one clinical and CDC *M. tuberculosis* strains, demonstrating different drug resistant profiles, were tested for sensitivity to gemfibrozil. Disks containing a given amount of GFZ were added to each of four quadrants of a plate. Five mls of Middlebrook agar were added to each quadrant, and the drug was allowed to diffuse throughout the agar in each quadrant overnight. 100 μls of a standard dilution of each *M. tuberculosis* strain were added to each quadrant, and the plates were incubated for three weeks at 37° C. No growth was indicated by (-). Fewer than 50 colonies were counted; (+) 50–100 colonies; (++) 100–200 colonies; (+++) 200–500 colonies; (++++) confluent growth.

FIG. 16. A *L. pneumophila* 20.1 kb DNA insert, expressed from pBSK, complements the envM *E. coli* ts mutant and confers sensitivity to GFZ at the restrictive temperature, 42° C., on low osmolarity LB plates. ts envM *E. coli* containing pBSK:2.1 were grown overnight in the presence of ampicillin, and then diluted $10^{-2}$. 100 μl of this dilution was mixed with 3 mls of melted 55° C. agar and poured over low osmolarity LB plates. Disks containing 5 mg of GFZ were added to the overlays, and the plates were incubated at 30° C. or 42° C. overnight. The diameter of the zones were measured to assess GFZ sensitivity.

DETAILED DESCRIPTION OF THE INVENTION

Figure 1:
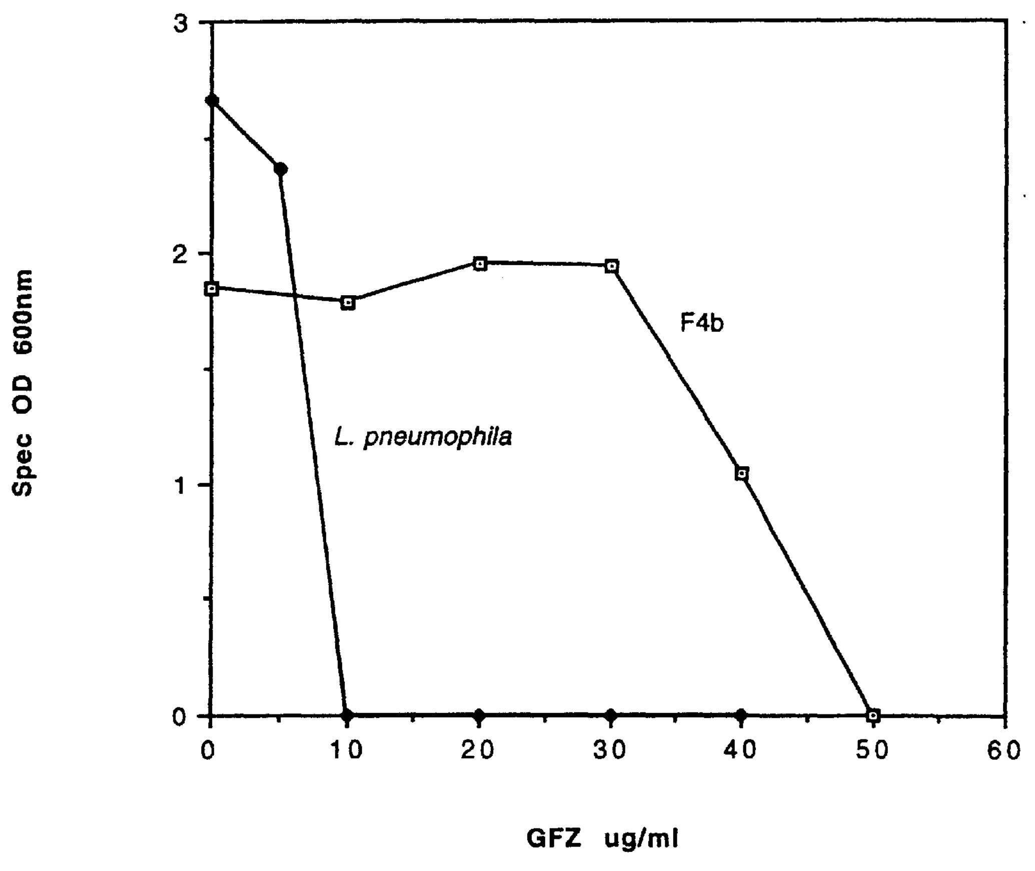
FIG. 1. MICs (minimal inhibitory concentration) for gemfibrozil were determined by incubating *L. pneumophila* or F4b with various concentrations of GFZ in AYE broth (microbiological media). Bacteria were present at an initial concentration of $1\times10^6$ CFU's (colony forming units)/ml. Growth was turbidimetrically assessed by determining the OD at 600 nm after a 48 hour incubation at 37° C.

The present invention provides for a method for inhibiting growth of a bacterium which consists essentially of contacting the bacterium with a compound having the structure

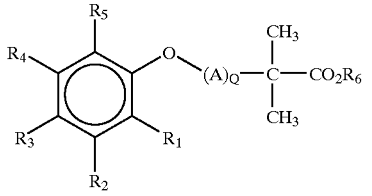

wherein each of $R_1$, $R_2$, $R_3$, $R_4$, $R_5$ and $R_6$ may be independently H, F, Cl, Br, I, —OH, —$OR_7$, —ON, —$COR_7$, —$SR_7$, —$N(R_7)_2$, —$NR_7COR_8$—$NO_2$, —$(CH_2)_pOR_7$, —$(OH_2)_pX(R_7)_2$, —$(CH_2)_pXR_7COR_8$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl; wherein $R_7$ or $R_8$ may be independently H, F, Cl, Br, I, —OH, —CN, —COH, —$SH_2$, —$NH_2$, —NHCOH, —$(CH_2)_pOH$, —$(CH_2)_pX(CH_2)$, —$(CH_2)_pXCOH$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl; wherein A may be —$N_2$—, —NH—, —C═C═$CH_2$—, —C≡C—$C_2$HOH—, —C≡C—$CH_2$—, —$CH_2$—$CH_2$—O—, —$CH_2$—$CH_2$—$CH_2$—O—, —S—, —S(═O)$_2$—, —C═O—, —C═O—O—, —NH—C═O—, —C═O—NH—; and wherein Q, p, n and x may independently be an integer from 1 to 10, or if Q is 1 A may be a ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and can optionally be interrupted 1 to 3 times by —O— or —S— or —N—; or a pharmaceutically acceptable salt or ester thereof, which compound is present in a concentration effective to inhibit growth of the bacterium. In this method, A may be an ($C_1$–$C_{10}$)-alkylene chain, ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and can optionally be interrupted 1 to 3 times by —O— or —S— or —N—. The ether linkage to the benzene ring may alternatively be —N—, —S— or —C—.

In one embodiment, the compound may include the following:

$R_1$=$R_4$=$CH_3$ or —OH, $R_2$=$R_3$=$R_5$=$R_6$=H or —OH,

A=$CH_2$, and Q=3.

In one embodiment, the compound may include the following:

$R_3$=Cl, $R_1$=$R_2$=$R_4$=$R_5$=$R_6$=—OH or H, and Q=0.

In anther embodiment, the compound may include:

$R_3$ =

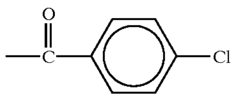

$R_6$=CH($CH_3$)$_2$, $R_1$=$R_2$=$R_4$=$R_5$=H or —OH, and Q=0.

In another embodiment, the compound may include:

$R_3$=Cl, $R_6$=$C_2H_5$, $R_1$=$R_2$=$R_4$=$R_5$=H or —OH, and Q=0.

The bacterium may include *Legionella pneumophila, Mycobacterium tuberculosis, Bacillus subtilis, Bacillus Megaterium, Pseudomonas Oleovorans, Alcaligenes eutrophus*, Rhodococcus sp., *Citrobacter freundi*, Group A Streptococcus sp., Coag neg *Staphylococcus aureus* or Nocardia sp. The bacterium may be *Legionella pneumophila*. The bacterium may be *Mycobacterium tuberculosis*. The bacterium may be Nocardia sp. The bacterium may be in a eukaryotic cell.

The concentration of the compound may be from about 5 μg/ml to about 100 μg/ml. In another embodiment, the concentration of the compound may be 20 μg/ml.

The present invention also provides a method for alleviating the symptoms of a bacterial infection in a subject which consists essentially of administering to the subject an amount of a compound having the structure

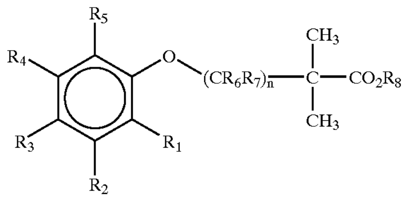

wherein each of $R_1$, $R_2$, $R_3$, $R_4$, $R_5$ and $R_6$ are as defined above. The ether linkage to the benzene ring may alternatively be —N—, —S— or —C—.

The method also includes use of a pharmaceutically acceptable salt or ester thereof, which compound is present in a concentration effective to inhibit bacterial growth and thus alleviate the symptoms of the bacterial infection in the subject.

The bacterial infection may be associated with a bacterium listed above. The subject may be a human or an animal. The bacterial infection may be associated with Leprosy, Brucella or Salmonella. The concentration of the compound may be from about 5 μg/ml blood of the subject to about 180 μg/ml blood of the subject. In one embodiment, the concentration of the compound may be 90 μg/ml blood of the subject. The administration to the subject may be oral.

The present invention also provides a method of inhibiting activity of Enoyl Reductase Enzyme which includes contacting the enzyme with a compound having the structure

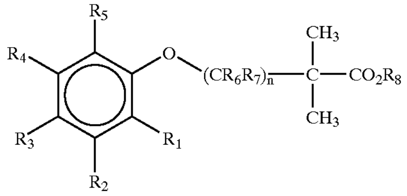

wherein each of $R_1$, $R_2$, $R_3$, $R_4$, $R_5$ and $R_6$ are as defined above. The ether linkage to the benzene ring may alternatively be —N—, —S— or —C—.

As used herein Enoyl Reductase Enzyme includes enzymes having enoyl reductase activity. Such enzymes may be bacterial enoyl reductases or eukaryotic enoyl reductases. Examples of bacterial enoyl reductases include those from the bacterium listed above. The enoyl reductase may be one of the enoyl reductases from *L. Pneumophila*. The enoyl reductase may be a gene product of a gene that hybridizes with moderate or high stringency with the envM gene.

The enzyme may be in a bacterium. The bacterium may be *Legionella pneumophila, Mycobacterium tuberculosis, Bacillus subtilis, Bacillus Megaterium, Pseudomonas Oleovorans, Alcaligenes eutrophus*, Rhodococcus sp., *Citrobacter freundi*, Group A Streptococcus sp., Coag neg *Staphylococcus aureus* or Nocardia sp. The bacterium may be *Legionella pneumophila*. The bacterium may be *Mycobacterium tuberculosis*. The enzyme may be in a cell. The cell may be a mammalian cell. The concentration of the compound may be from about 5 μg/ml to about 100 μg/ml. The concentration of the compound may be 20 μg/ml.

The present invention provides for a method of altering a pathway of fatty acid synthesis in a bacterium which comprises contacting the bacteria with a compound having the structure

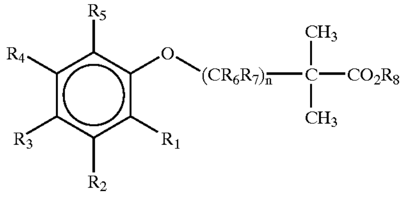

wherein each of $R_1$, $R_2$, $R_3$, $R_4$, $R_5$ and $R_6$ is as defined above. The ether linkage to the benzene ring may alternatively be —N—, —S— or —C—.

The present invention provides for a method for determining whether or not a bacterium is sensitive to a compound having the structure

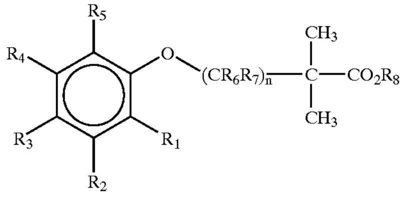

wherein each of $R_1$, $R_2$, $R_3$, $R_4$, $R_5$ and $R_6$ is as defined above. The ether linkage to the benzene ring may alternatively be —N—, —S— or —C—.

The present invention provides for a method of selecting a compound which is capable of inhibiting the enzymatic activity of enoyl reductase which includes:(A) contacting enoyl reductase with the compound; (B) measuring the enzymatic activity of the enoyl reductase of step (A) compared with the enzymatic activity of enoyl reductase in the absence of the compound, thereby selecting a compound which is capable of inhibiting the enzymatic activity of enoyl reductase. The compound may contact enoyl reductase at same site at which gemfibrozil contacts enoyl reductase. U.S. Pat. No. 5,422,372 discloses a method of increasing intracellular accumulation of hydrophilic anionic agents using gemfibrizol (gemfibrozil). U.S. Pat. No. 4,859,703 discloses lipid regulating compositions. U.S. Pat. No. 4,891, 220 discloses a method and composition for treating hyperlipidemia. The disclosures of these publications in their entireties are hereby incorporated by reference into this application in order to more fully describe the state of the art as known to those skilled therein as of the date of the invention described and claimed herein.

Another embodiment of the present invention is a kit which is capable of detecting the presence of a particular organism based on the sensitivity of the organism to gemfibrozil. The present invention provides for a kit for detecting the presence of one or more organisms in a sample which comprises: (a) an agar or solution medium suitable for growth of the organism; (b) a means for testing growth of each organism in the presence and absence of gemfibrizol such that the growth of the organism or lack thereof can be detected; (c) a means for determining the growth of the organism thus detecting the presence of one or more organisms in a sample. The kit may be in form of an assay, a screening kit or a detection kit.

In one embodiment the compound of the present invention is associated with a pharmaceutical carrier which includes a pharmaceutical composition. The pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings. The active ingredient can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like. The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

This invention is illustrated in the Experimental Details section which follows. These sections are set forth to aid in an understanding of the invention but are not intended to, and should not be construed to, limit in any way the invention as set forth in the claims which follow thereafter.

Experimental Details

EXAMPLE 1

*Lecionella Pneumophila* is Sensitive to Gemfibrozil

The original experimental objective, which led to the discovery of a gemfibrozil-inhibitable target in bacteria, involved the use of gemfibrozil (GFZ) to block a eukaryotic transporter in *Legionella pneumophila*-infected J774 macrophages. As a control experiment, *L. pneumophila* was incubated with the concentration of GFZ required to inhibit the eukaryotic transporter, and it was found that growth of *L. pneumophila* was suppressed, which was an unexpected result. A subsequent minimum inhibitory concentration (MIC) assay demonstrated that *L. pneumophila* grown in AYE medium was sensitive to GFZ concentrations as low as 10 μg/ml This was unexpected since gemfibrozil, a drug which therapeutically lowers triglycerides and raises HDL-cholesterol levels, has not been reported to have antimicrobial activity. The MIC assay (FIG. 1) was performed by preparing various concentrations of GFZ in AYE medium in test tubes. *L. pneumophila* was added to each tube to a final concentration of $1\times10^6$ CFUs/ml. After a 48 hour incubation at 37° C., growth was assessed turbidimetrically (OD at 600 nm). 10 μg/ml was the minimum GFZ concentration at which no growth occurred.

Figure 2:
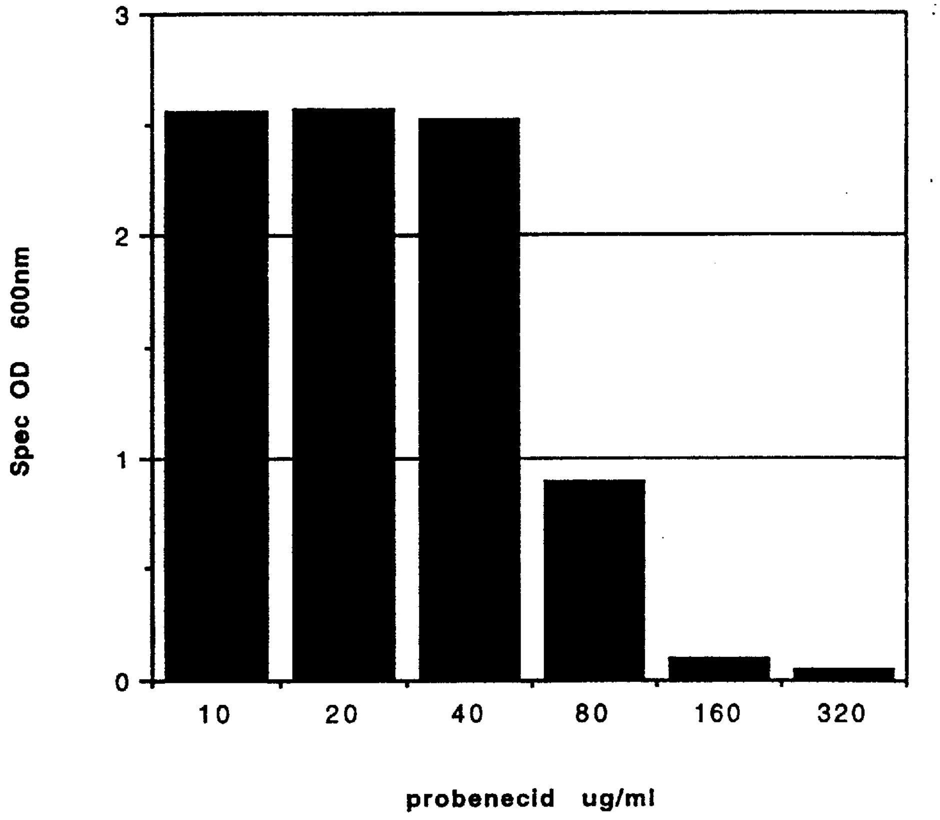
FIG. 2. MICs for probenecid were determined by incubating *L. pneumophila*, resuspended to $1\times10^6$ CFU's/ml, with various concentrations of probenecid in AYE broth. Growth was turbidimetrically assessed by determining the OD at 600 nm after 48 hours at 37° C.
Figure 3:
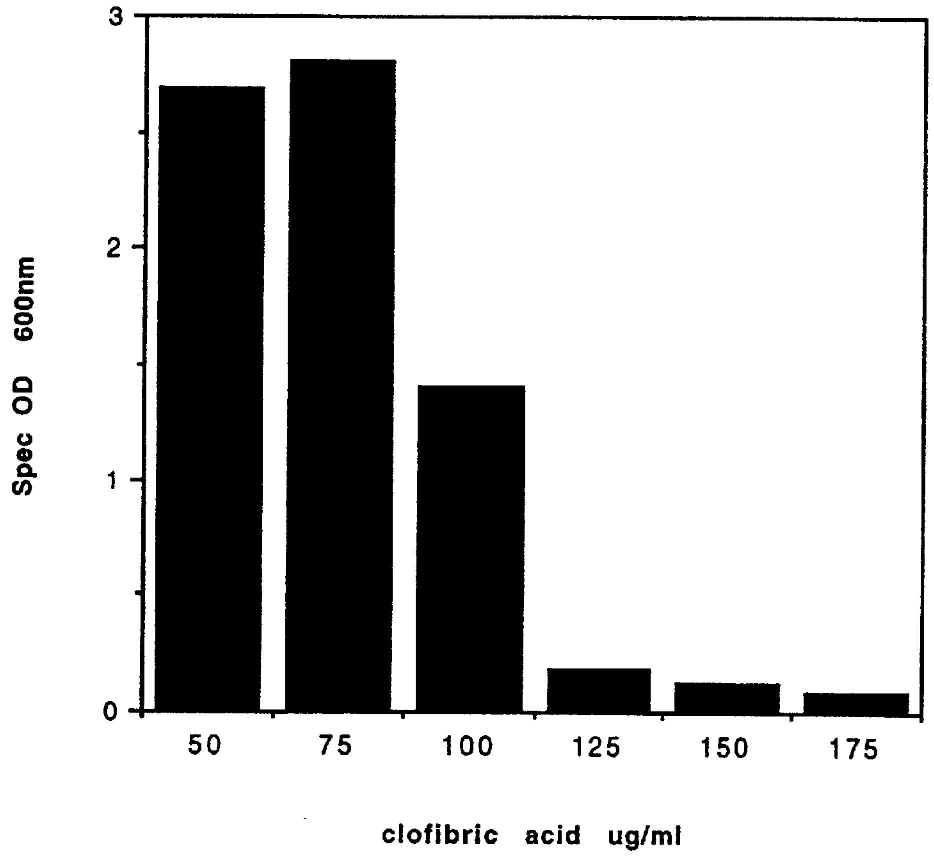
FIG. 3. MICs for clofibric acid were determined by incubating *L. pneumophila*, resuspended to $1\times10^6$ CFU's/ml, with various concentrations of clofibric acid in AYE broth. Growth was turbidimetrically assessed by determining the OD at 600 nm after 48 hours at 37° C.

MIC assays were then performed using clofibric acid, a related fibric acid, and probenecid, a drug which inhibits anion transporter activity in J774 cells. Probenecid had a MIC of 160 μg/ml in AYE (FIG. 2), while clofibric acid had an MIC of 125 μg/ml in AYE (FIG. 3). Both MICs were well above the 10 μg/ml seen with gemfibrozil. These results showed that gemfibrozil is especially effective as an inhibitor of *L. pneumophila.*

To determine whether gemfibrozil is bacteriocidal or bacteriostatic, *L. pneumophila* was grown for 48 hours in AYE medium containing varying concentrations of GFZ. Five microliter samples of each culture were plated on CYE agar plates. Growth was assessed after a four day incubation period at 37° C. The GFZ concentration at which no growth was seen on the CYE plates was 400 μg/ml. Therefore, GFZ at 10 μg/ml is bacteriostatic rather than bacteriocidal. Other commonly used antibiotics with bacteriostatic rather than bacteriocidal activity include chloramphenicol, the tetracyclines, erythromycin, and clindamycin.

Gemfibrozil Selectively Inhibits Bacteria that Synthesize Branched Chain Fatty Acids To determine whether the antimicrobial effect of gemfibrozil was specific for *L. pneumophila*, several strains of bacteria were screened using a zone of inhibition assay. This assay was performed by mixing 100 μl of a bacterial suspension with 3 mls of F-top agar heated to 50° C. and then pouring the mixture over a suitable agar-nutrient plate. When the overlay hardened, a disk containing GFZ was placed on the overlay, and the plate was incubated at the appropriate temperature until growth was seen. A clear zone surrounding the disk, or a "zone of inhibition," indicates that the drug on the disk inhibited bacterial growth. In general, the larger the zone of inhibition, the more potent the drug on the species of bacteria being tested. Assessing zones of inhibition is a quick way of screening many bacterial species for susceptibility. A wide variety of bacteria were then screened. The results of these screens indicated that all susceptible bacteria had branched chain fatty acids in their membranes, although not all bacteria with branched chain fatty acids were susceptible (FIG. 4).

The susceptibility of *Mycobacterium tuberculosis*, which contains very long, branched chain mycolic acids, was especially interesting given the prevalence of, and the mortality associated with, this organism. Therefore, 21 strains of *M. tuberculosis* were tested, including pan-sensitive and multidrug resistant strains. Sensitivity of *M. tuberculosis* to GFZ was assessed by a placing a gemfibrozil-containing disk in the bottom of one of four quadrants of a petri dish. Five milliliters of Middlebrook agar were then poured over the disk or disks in each quadrant, and the plates were incubated overnight at room temperature to allow diffusion of the drug throughout the quadrant. A saline suspension containing *M. tuberculosis* at a McFarland standard of two was prepared, and then diluted $10^{-2}$. 100 μl of this dilution was added to each quadrant, and the plates were incubated at 37° C. for three weeks. The presence or number of colonies in each of the quadrants then was assessed. The GFZ concentration at which no growth was seen was considered to be the MIC. All strains were susceptible to concentrations between 100 μg/ml and 200 g/ml of gemfibrozil (FIG. 5). Although the inhibitory concentration is higher than the concentration of gemfibrozil used in humans treated for hyperlipidemia (15–30 μg/ml), all 21 strains were susceptible to GFZ within a two-fold concentration range. No greater than a two fold difference in sensitivity was seen. This suggests that none of the presently evolved antibiotic resistance mechanisms affect sensitivity to gemfibrozil, and that it has a novel target site.

Development of a Mutant of *L. pneumophila* with Increased Resistance to GFZ

The discovery that *L. pneumophila* was sensitive to GFZ necessitated the development of a *L. pneumophila*-derived GFZ-resistant mutant that could be used in the transporter experiments. Efforts to obtain spontaneous mutants by plating $10^8$ wild type *L. pneumophila* on CYE agar plates containing GFZ were unsuccessful. Therefore, the alkylating agent ethyl methane sulfonate (EMS) was used to mutagenize the DNA of *L. pneumophila* cultures. Although attempts to generate a fully resistant mutant were unsuccessful, development of a semi-resistant mutant was successful. The mutant, F4b, had an MIC of 50 μg/ml GFZ. Similar attempts to generate a *Bacillus subtilis* gemfibrozil-resistant mutant, by either spontaneous mutagenesis or by EMS mutagenesis were completely unsuccessful. The inability to develop high-level gemfibrozil-resistant mutants in either species of bacteria suggests that gemfibrozil's target may be an essential gene product in these bacteria.

GFZ Induces the Accumulation and Expansion of Lipid-Like Inclusion Bodies in *L. pnuemophila*

Figure 6A:
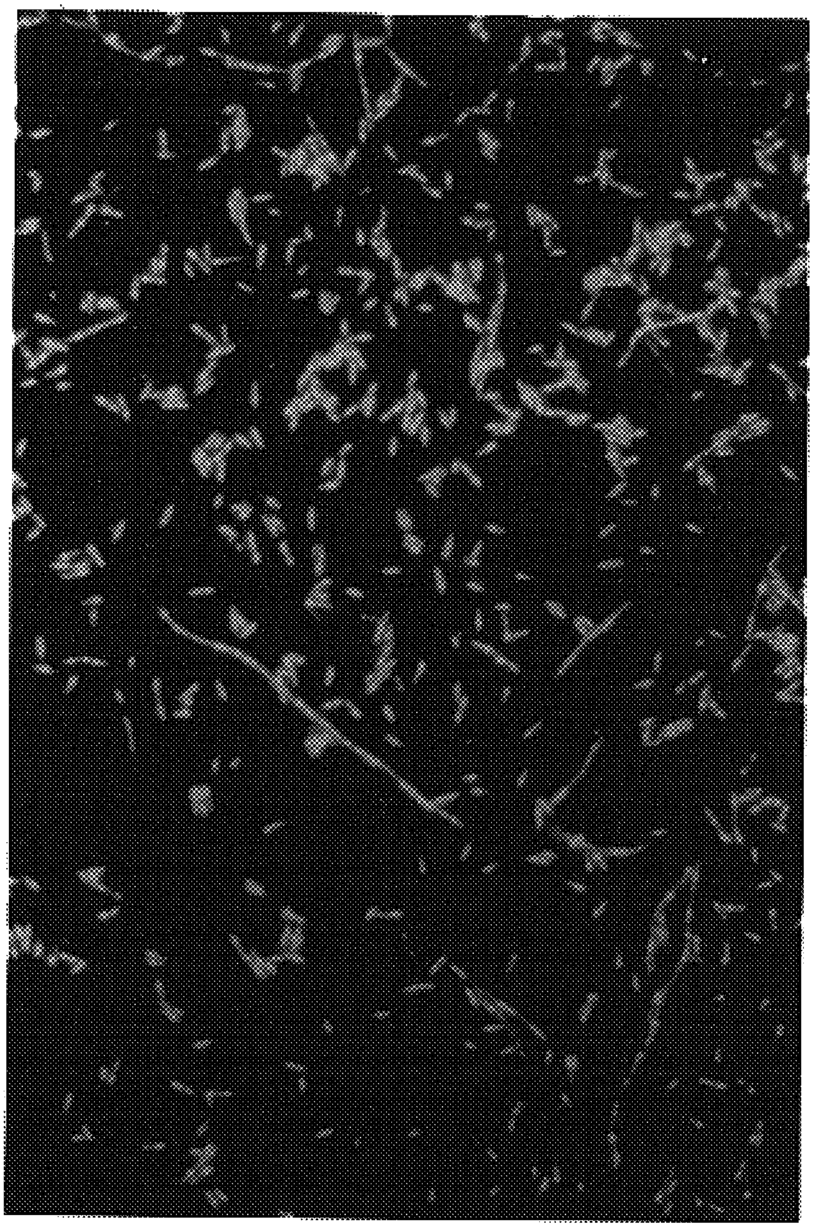
FIGS. 6A–6B. GFZ induces large distending inclusions in a subpopulation of *L. pneumophila* grown in the presence of a subinhibitory concentration of GFZ. (A) Stationary phase *L. pneumophila*, grown in AYE, stained with Nile Blue A. Numerous nondistending granules present in the majority of the bacteria. (B) Stationary phase *L. pneumophila*, grown in AYE(+GFZ), stained with Nile Blue A. Numerous large, distending granules present in a subpopulation of the bacteria, other bacteria demonstrate few to no inclusions.
Figure 6B:
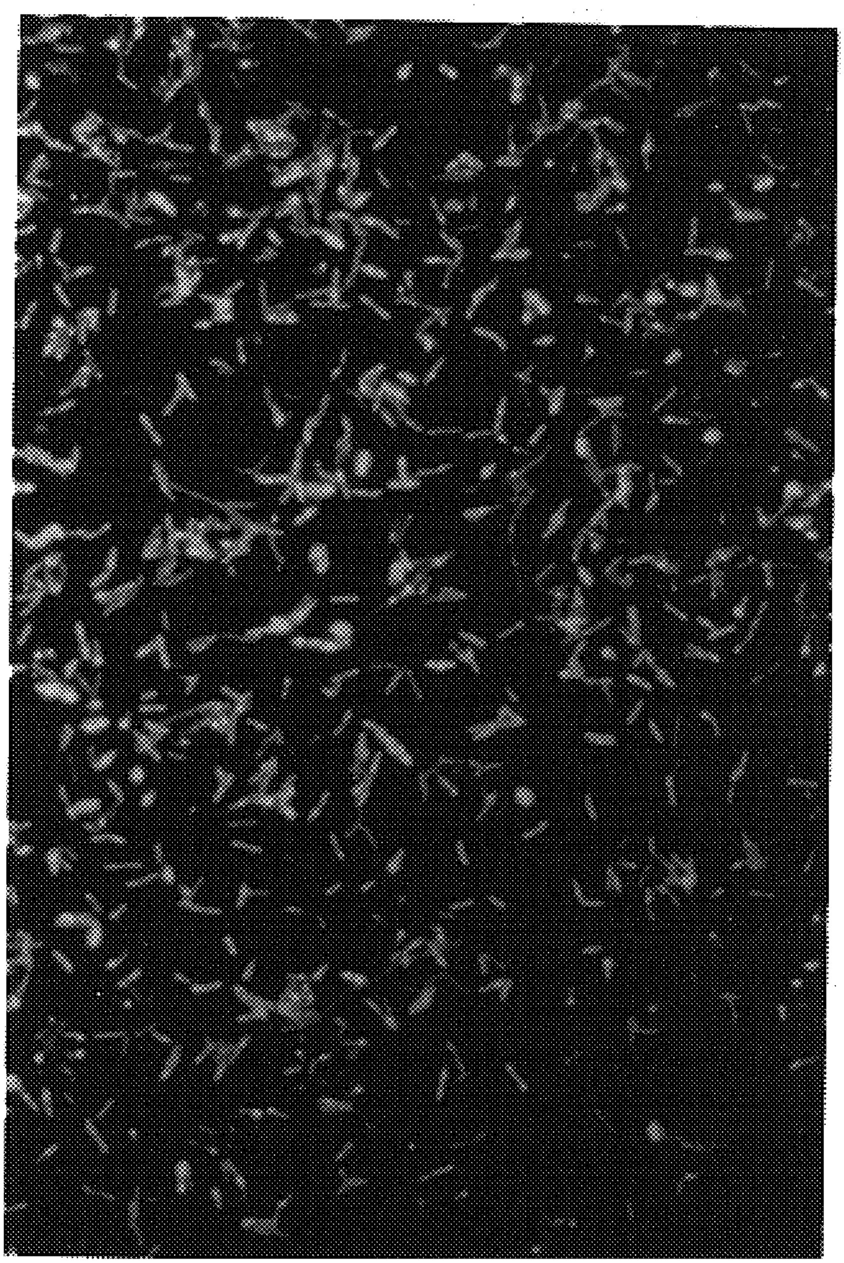

Since the mechanism of action and target of GFZ was still unclear, Nile Blue A fluorescence was used to assess the morphology of *L. pneumophila* grown in the presence of sub-inhibitory concentrations of the drug. Nile Blue A is a water soluble basic oxazine dye that fluoresces at 460 nm. This dye has greater specificity and higher affinity than Sudan Black for polyhydroxybutyrate (PHB) and does not stain glycogen and polyphosphate inclusions. As wild type *L. pneumophila* enter stationary phase in the absence of gemfibrozil, they tend to elongate and accumulate numerous non-distending granules (FIG. 6A). However, staining of *L. pneumophila* grown to stationary phase in the presence of GFZ demonstrated that there was a subpopulation of bacteria with few to no inclusions, and a subpopulation of bacteria distended by large granules (FIG. 6B). The ability of Nile Blue A to stain these granules indicates that they are composed of PHB or other types of polyhydroxy alkanoic acids (PHAs).

PHAs are natural polyesters of B-hydroxyacyl monomer units, three to fourteen carbons in length. Hydroxyacyl monomer units can be utilized by bacteria as a carbon source, as precursors in fatty acid synthesis, or, in some bacterial species, stored as PHA in inclusion bodies. PHA forming species include *Bacillus megaterium, Pseudomonas oleovorans, Psuedomonas aeruginosa, Alcaligenes eutrophus*, and some Rhodococcus sp., Corynebacterium sp., and Nocardia sp. strains. *P. aeruginosa* is not susceptible to GFZ, but does form PHA granules. Therefore, the ability to form PHA inclusions does not seem to be correlated with susceptibility. However, the ability of some species, such as *P. oleovorans*, to incorporate branched chain hydroxyacyl fatty acid precursors into PHA, suggests that the distending granules seen in *L. pneumophila* exposed to GFZ might be composed of branched chain fatty acid precursors. Since only bacteria that synthesize branched chain fatty acids are susceptible, it is possible that a metabolic block in branched chain fatty acid synthesis induced by GFZ would result in the accumulation of precursors. In bacteria capable of producing PHA inclusions, accumulation of precursors might result in their packaging and storage in PHA granules.

Figure 7:
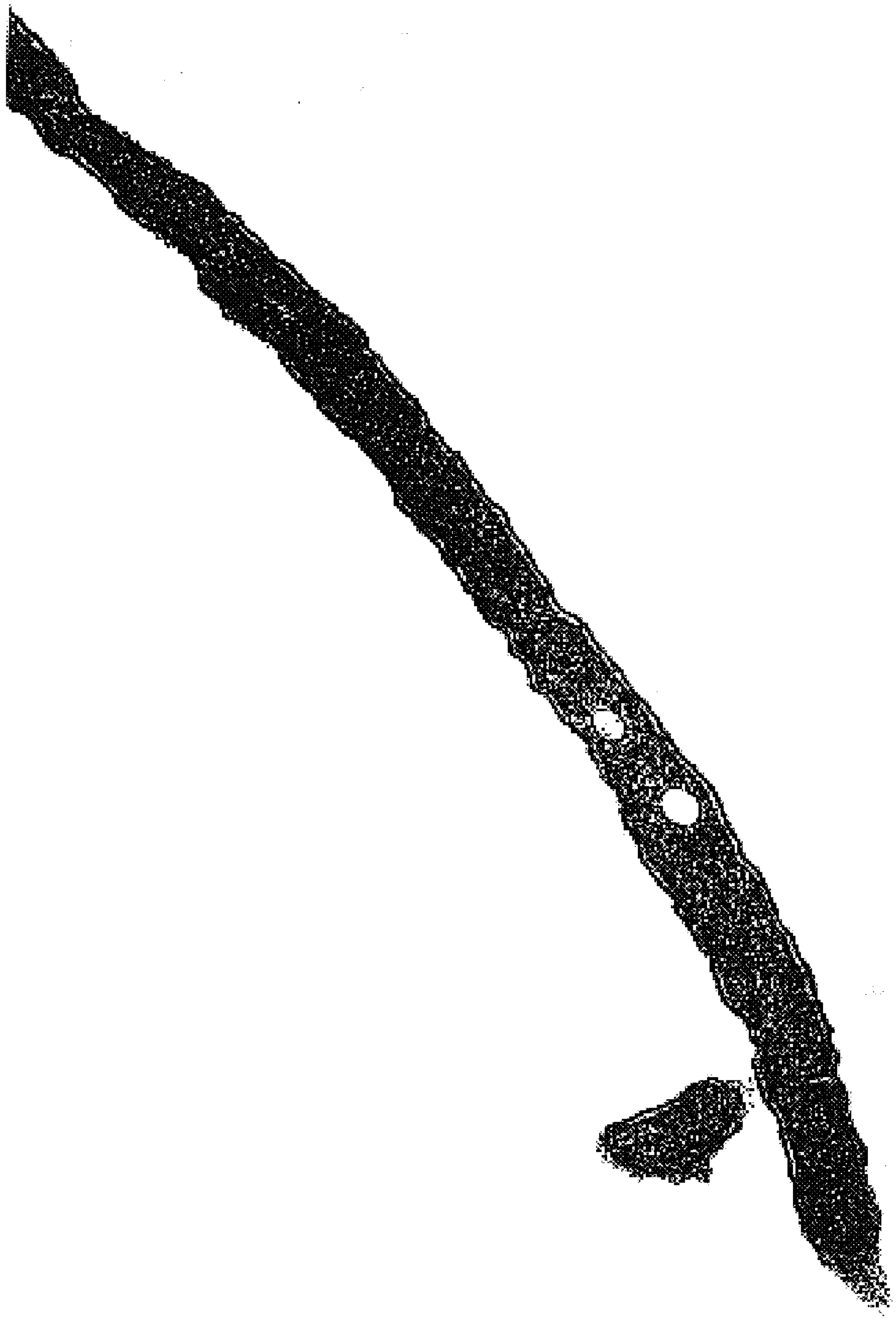
FIG. 7. Electron micrograph, 20,000×, of *L. pneumophila* grown to log phase on a CYE plate. Note the presence of small, non-distending inclusions.
Figure 8:
FIG. 8. Electron micrograph, 20,000×, of *L. pneumophila* grown on a CYE plate containing an inhibitory concentration of GFZ. Note the presence of large, distending inclusions in a subpopulation of the bacteria, and the absence of inclusions in other bacteria.

Experiments utilizing electron microscopy yielded confirmed the fluorescence data. Log phase *L. pneumophila* grown on CYE agar plates with no gemfibrozil, contained one or two small lipid-like inclusions (FIG. 7). In contrast, *L. pneumophila* and *L. pneumophila* mutants that were partially resistant to GFZ, grown on CYE-GFZ drug plates, appeared as either bacilli without inclusions, or, as short, swollen bacilli (about 2× the normal diameter) packed with large inclusions (FIG. 8). These results suggested that GFZ induced the accumulation of a metabolic precursor that was incorporated into the inclusion bodies seen in susceptible *L. pneumophila.*

Figure 9A:
FIGS. 9A, 9B, 9C and 9D. Demonstration of an intermediate phenotype during GFZ-induced inclusion development in *L. pneumophila*. Electron micrographs, 8,000×, of pelleted *L. pneumophila* and F4b grown in AYE broth in the presence or absence of GFZ 85 μg/ml for 4.5 hours. *L. pneumophila* demonstrates increased numbers of inclusions, while F4b, the GFZ semi-resistant mutant, does not. (A) *L. pneumophila*; no GFZ (B) F4b; no GFZ (C) *L. pneumophila*; GFZ 85 μg/ml (D) F4b; GFZ 85 μg/ml.
Figure 9B:
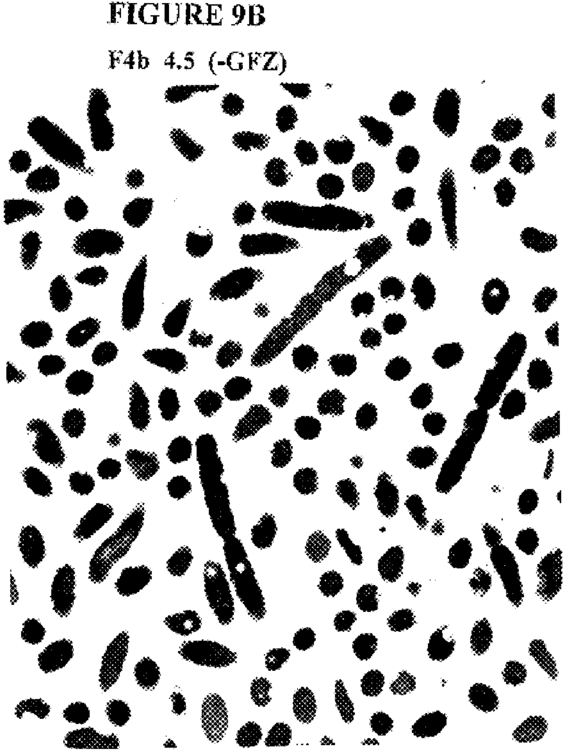
Figure 9D:
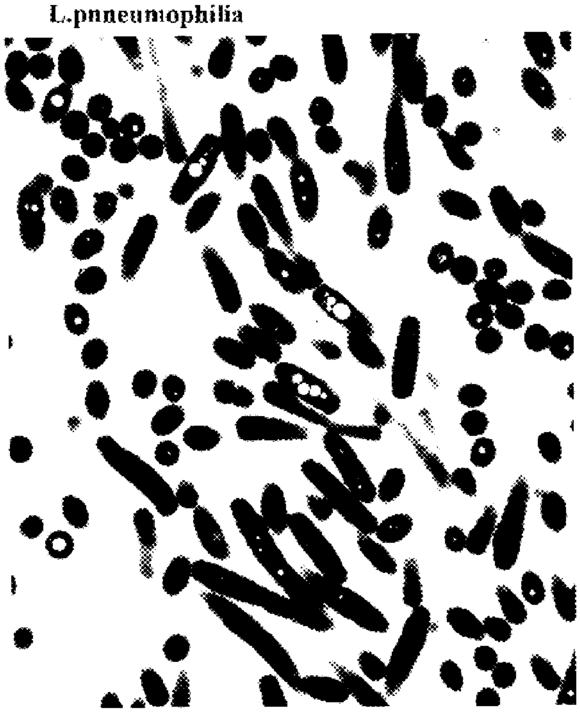
Figure 9C:
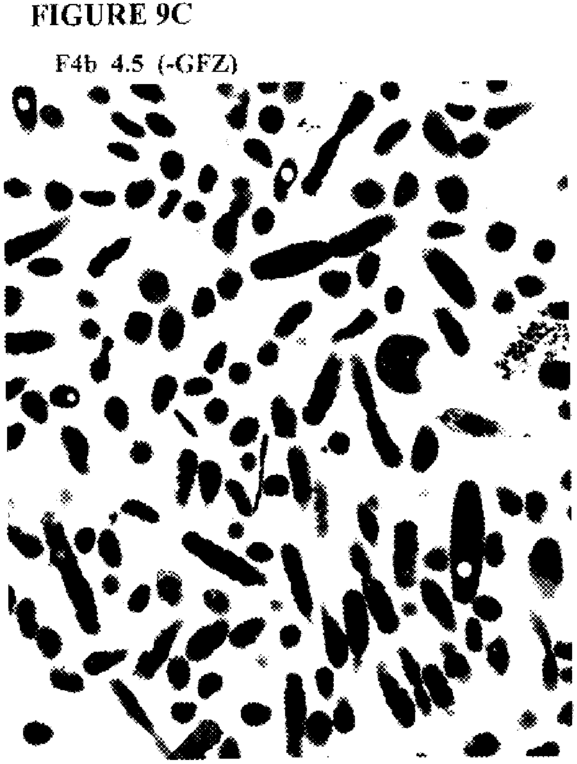

A second EM experiment compared log phase growth of *L. pneumophila* and the GFZ resistant F4b mutant in AYE broth, in the presence and absence of a sub-inhibitory concentration of gemfibrozil. The concentration of GFZ used inhibited *L. pneumophila* growth in AYE, but did not inhibit F4b growth in AYE. Four and one half hours after the addition of GFZ to the log phase AYE cultures, *L. pneumophila* (+GFZ) (FIG. 9C) accumulated granules, while *L. pneumophila* (−GFZ) (FIG. 9A) did not. In contrast, there was no apparent difference in the number or size of inclusions present in F4b in the presence (FIG. 9D) or absence (FIG. 9B) of GFZ. This experiment demonstrated an intermediate stage in inclusion accumulation in wild type *L. pneumophila.*

In summary, the presence of gemfibrozil induces the accumulation of inclusions in *L. pneumophila*, and, induces large, distending inclusions in a subpopulation of these susceptible bacteria. Additionally, the inclusions have a lipid-like morphology by EM, and stain with Nile Blue A, indicating that they may be composed of PHAs. These results suggest that the large, distending inclusions may be due to the accumulation of a precursor involved in fatty acid metabolism.

Gemfibrozil Affects the Fatty Acid Composition of *L. pneumophila*, but not its Semi-Resistant Derivative, F4b.

Figure 10A:
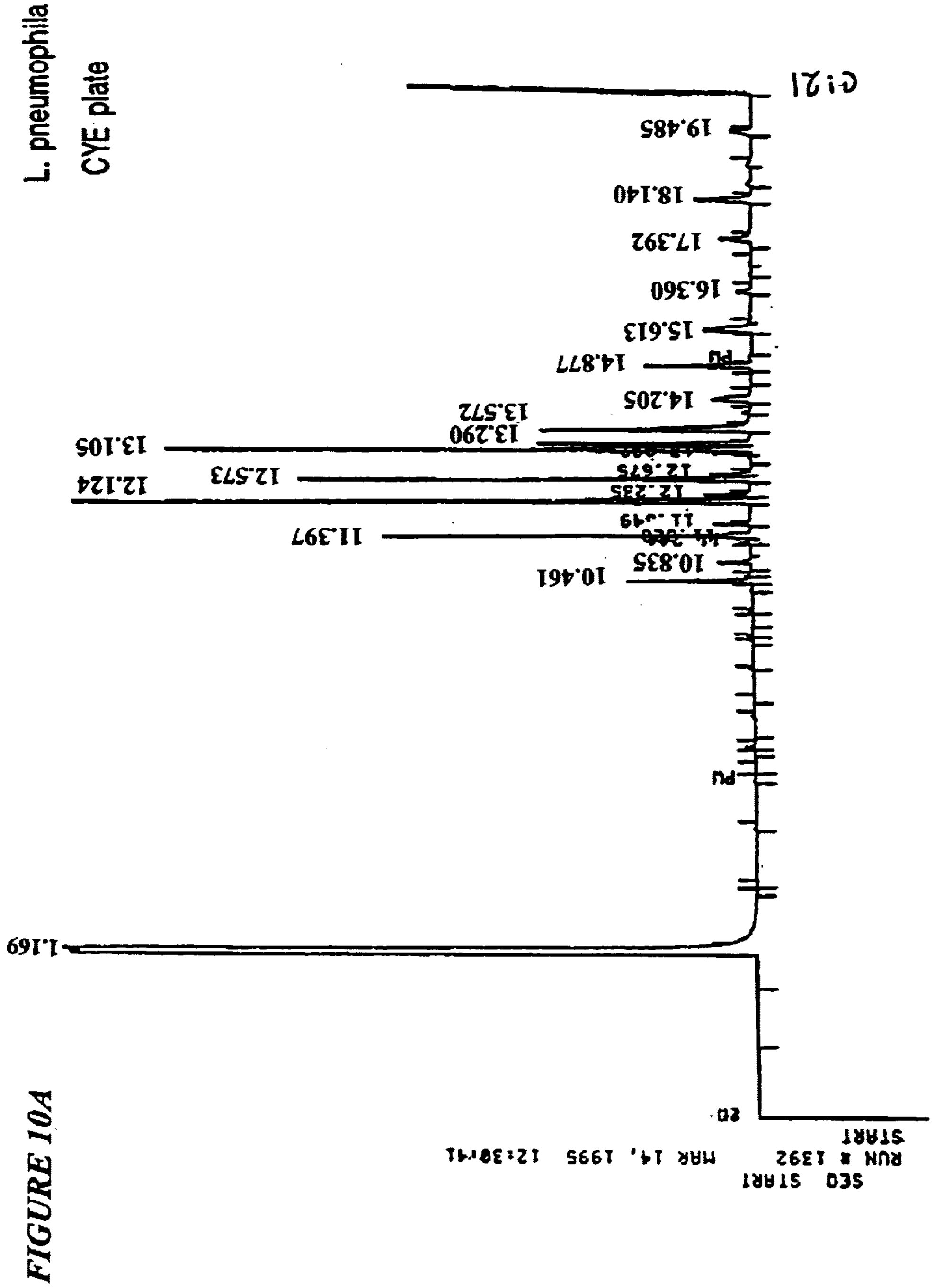
FIGS. 10A, 10B, 10C and 10D. Fatty acid compositions of wild type *L. pneumophila*, and the GFZ semi-resistant mutant F4b, grown in the presence or absence of a subinhibitory concentration of gemfibrozil. Fatty acid compositions were assessed by saponifying, methylating, and extracting the fatty acids present in the bacteria scraped from the plates, and then injecting the methylated fatty acids into a gas chromatograph. A step temperature program was used such that as the temperature was increased, sequentially longer chain fatty acids were released from the column and detected as peaks on the chromatogram. (A) Wild type *L. pneumophila* grown on CYE plates in the absence of GFZ (B) Wild type *L. pneumophila* grown on CYE(GFZ 30 μg/ml) plates; peaks that have decreased in size are marked by arrows, new peaks are marked by dots. (C) F4b grown on CYE plates in the absence of GFZ (D) F4b grown on CYE(GFZ 30 μg/ml) plates.
Figure 10B:
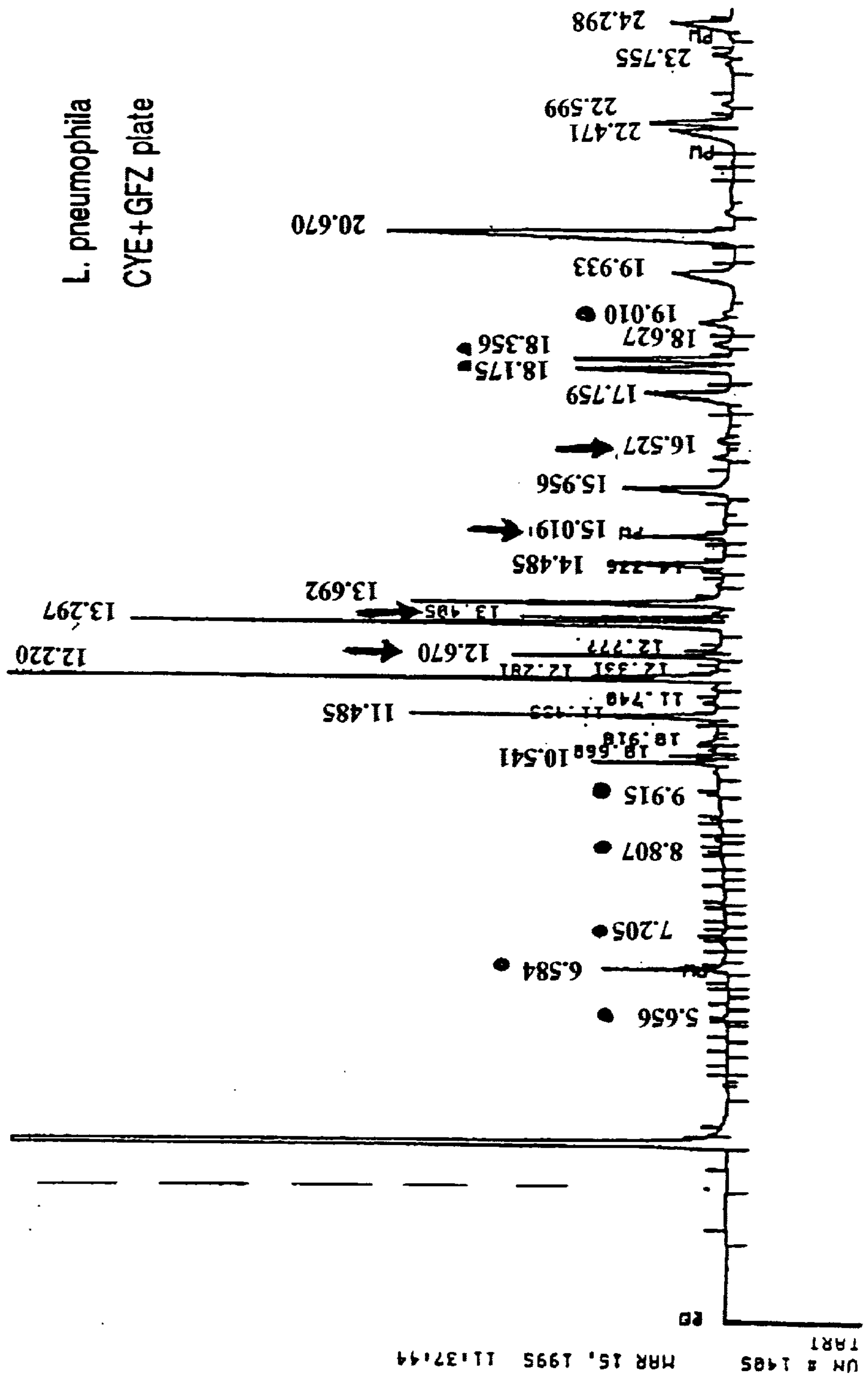
Figure 10C:
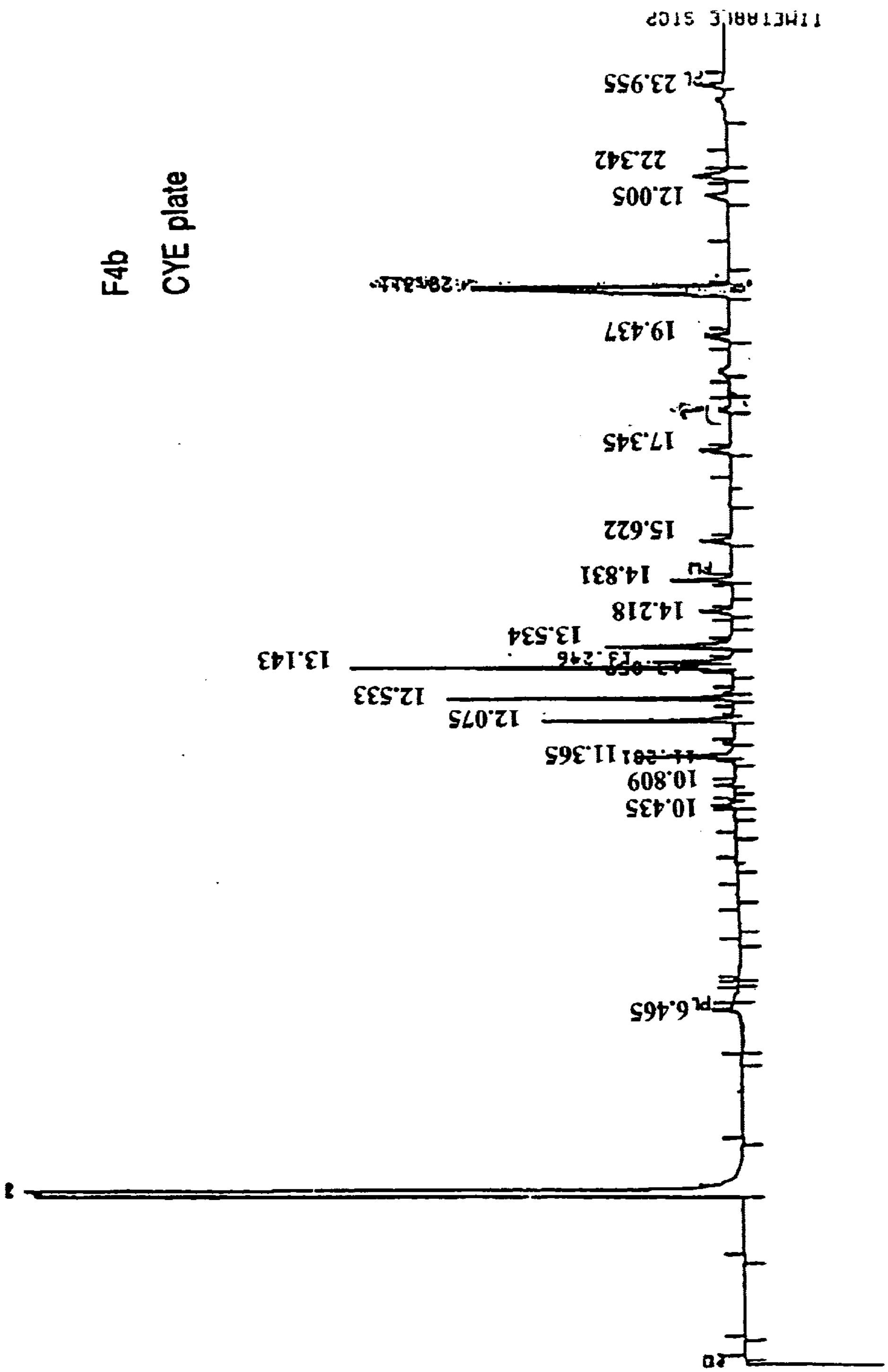

If GFZ affects enzyme(s) involved in fatty acid synthesis, and inhibition of this enzyme results in the accumulation of fatty acid precursors, then exposure to GFZ should alter the fatty acid composition of GFZ-susceptible bacteria. To address this possibility, gas chromatograhy was used to compare the fatty acid profiles of *L. pneumophila* (FIG. 10A) and the semi-resistant mutant, F4b (FIG. 10C), grown in the presence and absence of sub-inhibitory concentrations of gemfibrozil. Base hydrolysis was used to saponify the fatty acids, which were then methylated, extracted, and injected into a gas chromatograph. A step temperature program was used such that as the temperature increased, progressively longer chain fatty acids were released from the column and detected as peaks on the chromatograph. The presence of gemfibrozil resulted in decreased peak areas for several typical *L. pneumophila* fatty acids, and, the appearance of several new fatty acids (FIG. 10B). This indicated that GFZ inhibited the synthesis of several “typical” fatty acids and suggested that “new” fatty acids accumulate as a result of a metabolic backup. In FIG. 10B, fatty acid peaks which decreased in the presence of GFZ are marked by downward arrows, new peaks which appeared in the presence of GFZ are marked by dots.

Figure 10D:
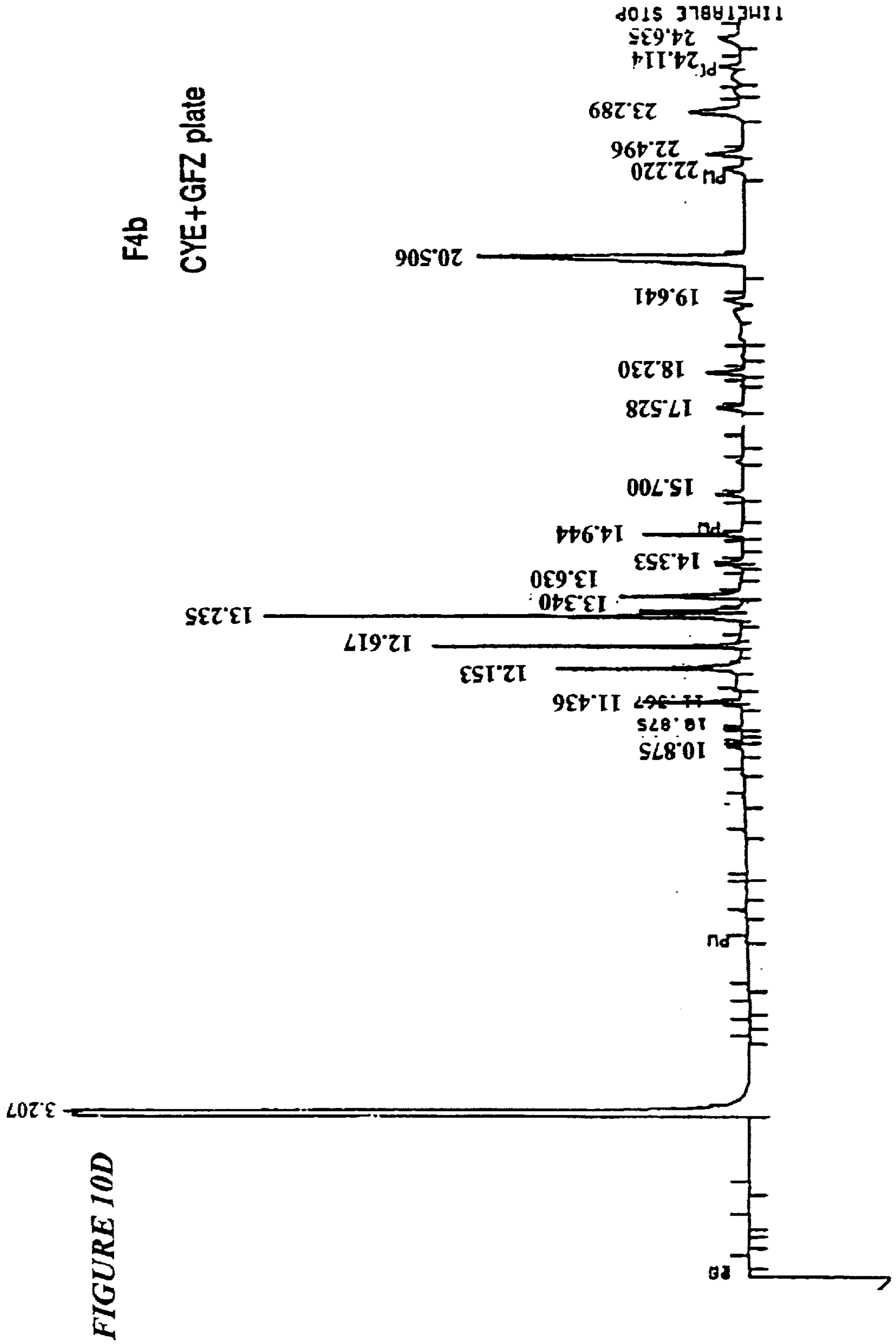

Importantly, the presence of gemfibrozil did not affect the fatty acid profile of F4b (FIG. 10D). This indicates that F4b resistance may be mediated by an enzyme with a lower affinity for GFZ, and, that this enzyme is involved in fatty acid synthesis. Additionally, the fatty acid profile of F4b looked quite different from that of wild type *L. pneumophila*, in that it had fewer peaks than *L. pneumophila*. Although no new peaks were detected in F4b, there were fewer peaks, and those peaks which were present, were present in different proportions than in *L. pneumophila*. The identity of the fatty acids has not been determined in the chromatograms since many of them were not present in the standard. A disappointing limitation was the inability to detect or identify fatty acids less than twelve carbons long using this system. Identification of shorter chain fatty acids may be useful in determining the identity of the gemfibrozil-induced inclusions.

Isoniazid (INH)-Resistant F4b Revertants

Figure 11:
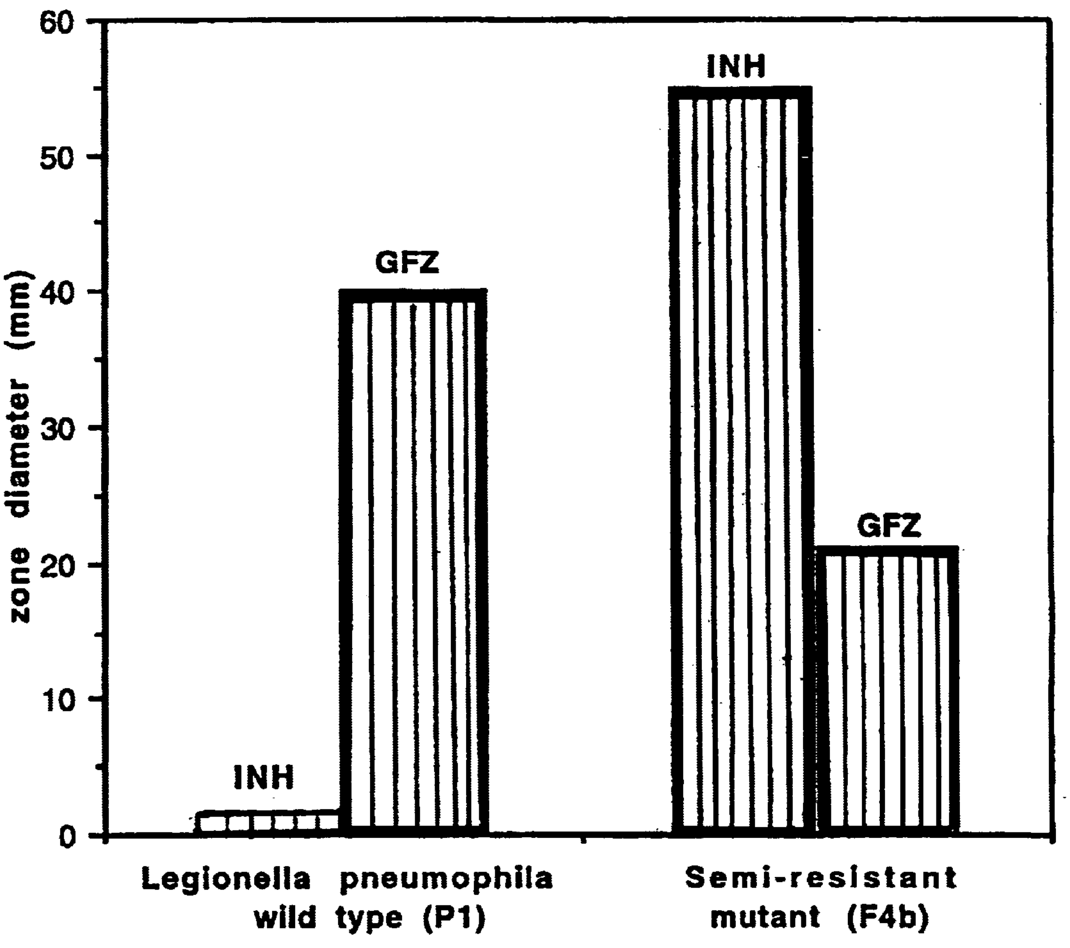
FIG. 11. Sensitivity of *L. pneumophila* and F4b to INH. Bacterial overlays on CYE agar plates were prepared by adding $2\times10^7$ bacteria to 3 mls of melted 50° C. agar and pouring the mixture over 15 ml CYE agar plates. Sterile disks containing 1 mg of INH, or 250 μg of GFZ were added to the overlays, and the plates were incubated for four days. Sensitivity was assessed by measuring the diameter of the zone of inhibition, the area where bacterial growth was inhibited, surrounding the drug disks.

Since there is significant evidence supporting the hypothesis that gemfibrozil affects fatty acid metabolism in *L. pneumophila, L. pneumophila* and F4b were tested for sensitivity to isoniazid, a tuberculostatic drug which targets an enoyl reductase involved in mycolic fatty acid synthesis in *M. tuberculosis*. While wild type *L. pneumophila* showed no sensitivity to isoniazid, the semi-resistant mutant, F4b, was sensitive (FIG. 11). This indicated that the mutation responsible for GFZ resistance might also have conferred isoniazid sensitivity.

Figure 12:
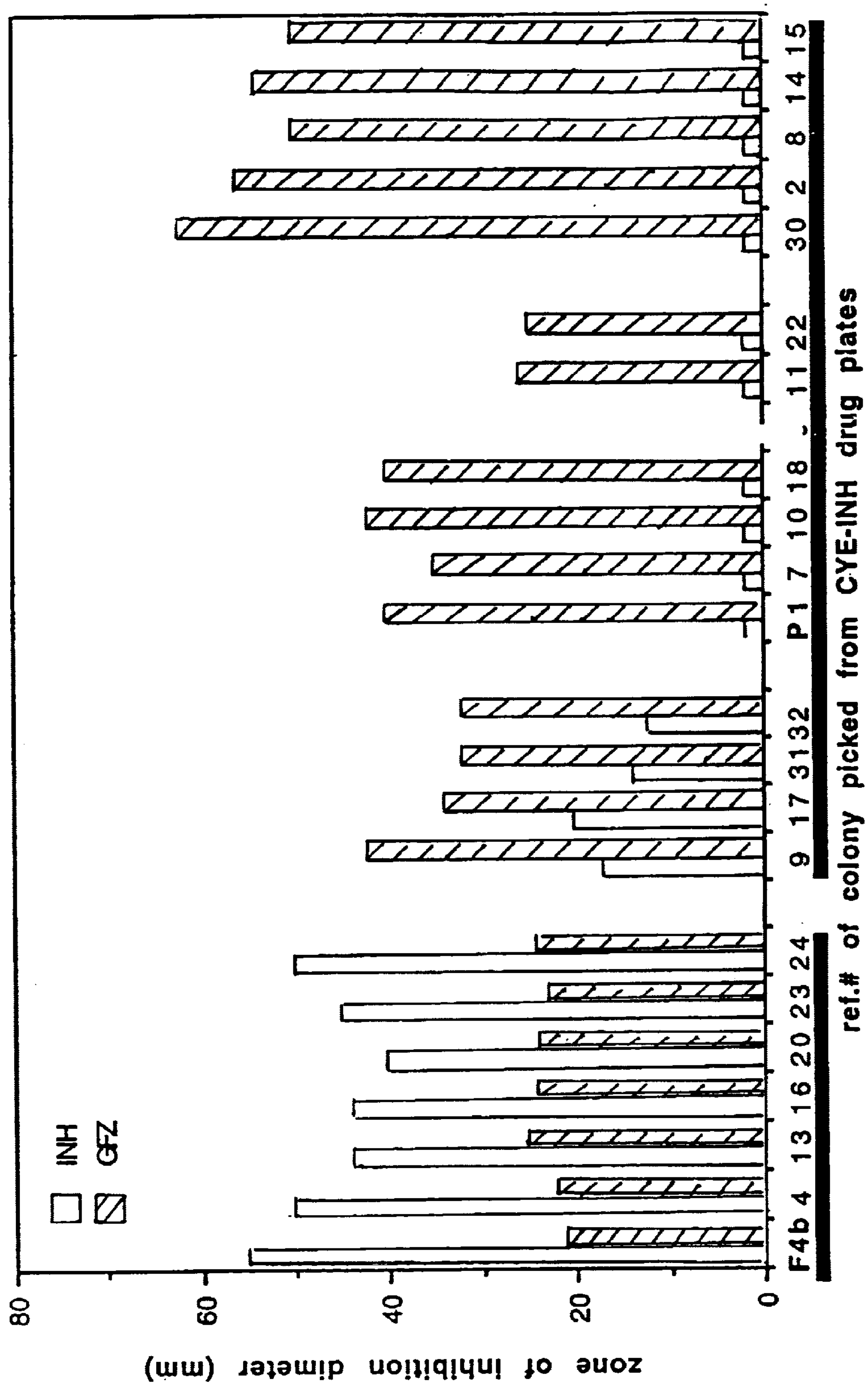
FIG. 12. Demonstration of inverse relationship between GFZ sensitivity and INH sensitivity using INH-resistant F4b revertants. INH-resistant F4b revertants were obtained by adding F4b to CYE-INH drug plates (400 μg/ml) and screening for spontaneous INH-resistant mutants after four days of incubation at 37° C. INH resistant colonies, which arose at a frequency of $1/10^{-7}$, were picked, passed non-selectively three times on CYE, and then tested for GFZ and INH sensitivity using the zone of inhibition assay. The assay was performed by adding $2\times10^7$ bacteria to 3 mls of melted 55° C. agar, pouring the mixture over 15 ml CYE plates, and then adding 1 mg INH sterile disks and 250 μg GFZ sterile disks to the overlays. After a four day incubation at 37° C., the diameter of the zones of inhibition were measured. The colonies indicated by the left bar under the histogram retained the parental phenotype and thus were not revertants. The colonies indicated by the right bar under the histogram regained GFZ sensitivity as INH sensitivity was lost.

To see whether isoniazid sensitivity and gemfibrozil resistance had a reciprocal relationship (which would imply that they share the same target enzyme) INH-resistant derivatives of F4b were isolated. To do this, the isoniazid-sensitive, gemfibrozil-resistant, F4b strain was plated out on CYE drug plates containing isoniazid 400 jig/ml, and screened for spontaneous mutants resistant to isoniazid. Single colonies of spontaneous mutants arose at a rate of $1\times10^{-7}$. Several of these colonies were picked and purified by passage on nonselective CYE agar plates. The purified F4b derived INH-resistant strains were then tested for both isoniazid sensitivity and gemfibrozil sensitivity using the zone of inhibition assay (FIG. 12).

The colonies indicated by the left bar under the histogram maintained the parental, F4b, INH-sensitive GFZ-resistant phenotype, indicating that they were not true INH-resistant revertants. Since the purification was nonselective, contaminating parental F4b bacteria may form colonies which are picked for father passage. Also, isoniazid-resistance due to up regulation of an enzyme, rather than a genetic-mediated resistance, would be lost in the absence of a selective pressure. Therefore, when the "purified" colonies are retested for isoniazid sensitivity, one expects to see colonies with either the parental phenotype or a genetically-mediated isoniazid-resistance phenotype.

The colonies indicated by the right bar under the histogram regained GFZ sensitivity as INH sensitivity was lost. The reciprocal relationship between gemfibrozil sensitivity and isoniazid sensitivity in these revertants, indicates that both drugs have the same target enzyme but different target sites. The mutation which allows gemfibrozil resistance (and probably affects substrate recognition) may result in a conformational change exposing an isoniazid sensitive site. In Mycobacteria sp., the INH target, enoyl reductase, is encoded by inhA. Since GFZ appears to target an enzyme which can be made INH-sensitive, it is probably targeting an InhA homologous enzyme in *L. pneumophila.*

EXAMPLE 2

Figure 13:
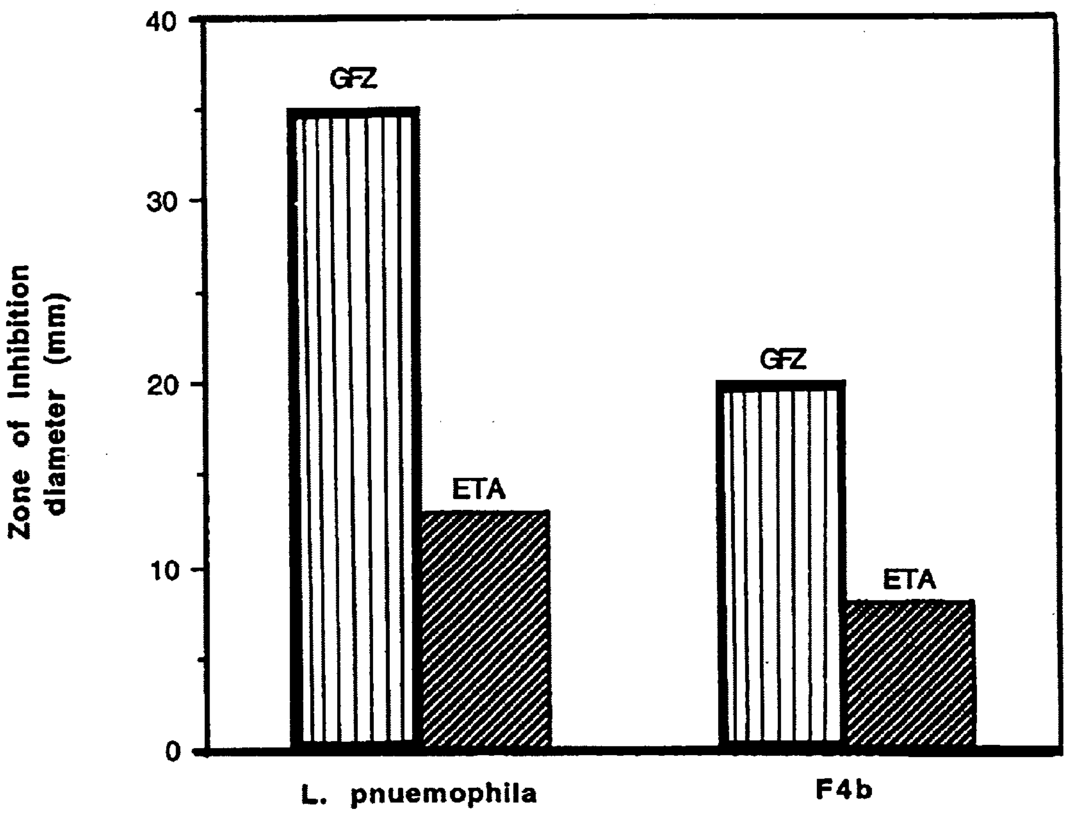
FIG. 13. Sensitivity of *L. pneumophila* and F4b to ethionamide. Ethionamide resistance correlates with GFZ resistance in the *L. pneumophila*-derived mutant F4b. Sensitivity was assessed by measuring the diameter of the zone of inhibition in bacterial overlays surrounding 250 μg GFZ disks, or 500 μg ethionamide disks.

Additional Evidence for an InhA Homologous Target: Differences in Sensitivity to Ethionamide Ethionamide sensitivity provided additional evidence to support the hypothesis that the target gene in Legionella is homologous to the InhA gene. Ethionamide is a second line anti-tuberculosis drug which is thought to target the same enzyme as isoniazid in Mycobacteria sp. If GFZ is targeting the homologous enzyme in *L. pneumophila*, and F4b resistance to GFZ is mediated by a conformational change in the target enzyme, then sensitivity to ethionamide might also differ between *L. pneumophila* and F4b. Using a zone of inhibition assay, wild type *L. pneumophila* was twice as sensitive to ethionamide as F4b (FIG. 13).

Growth of Intracellular *L. pneumophila* is Inhibited by Gemfibrozil

Since bacterial species such as *L. pneumophila* and *M. tuberculosis* are primarily intracellular pathogens, for an antibiotic to be effective it must affect bacterial growth within host white blood cells. For example, the drug must permeate macrophages, and have access to the intracellular compartment containing the pathogen. It is equally important that factors or nutrients provided by the host white blood cells do not bypass the metabolic step blocked by the drug.

GFZ at 100 μg/ml partially inhibited growth of *L. pneumophila* in human monocytes, macrophages, HL-60 cells (a human leukemic cell line), and J774 cells (a mouse macrophage cell line). In these experiments, monolayers of human or mouse cells were infected for two and one half hours with wild type *L. pneumophila* or the GFZ semi-resistant Legionella mutant F4b and then washed to remove extracellular bacteria. GFZ was added to the medium at a concentration of 100 μg/ml, and the cells were incubated at 37° C. Bacteria were assayed at the specified time points by lysing the cells in each monolayer, combining the cell lysate with the medium from the same well, and plating for CFU's on CYE agar plates. Since *L. pneumophila* and F4b do not replicate in the medium, any growth inhibition measured will be due to inhibition of intracellular replication by GFZ. The presence of GFZ (100 μg/ml) did not affect HL-60 cell viability after a 5 day period, so inhibition of intracellular *L. pneumophila* by GFZ is not due to decreased host cell viability.

Figure 14A:
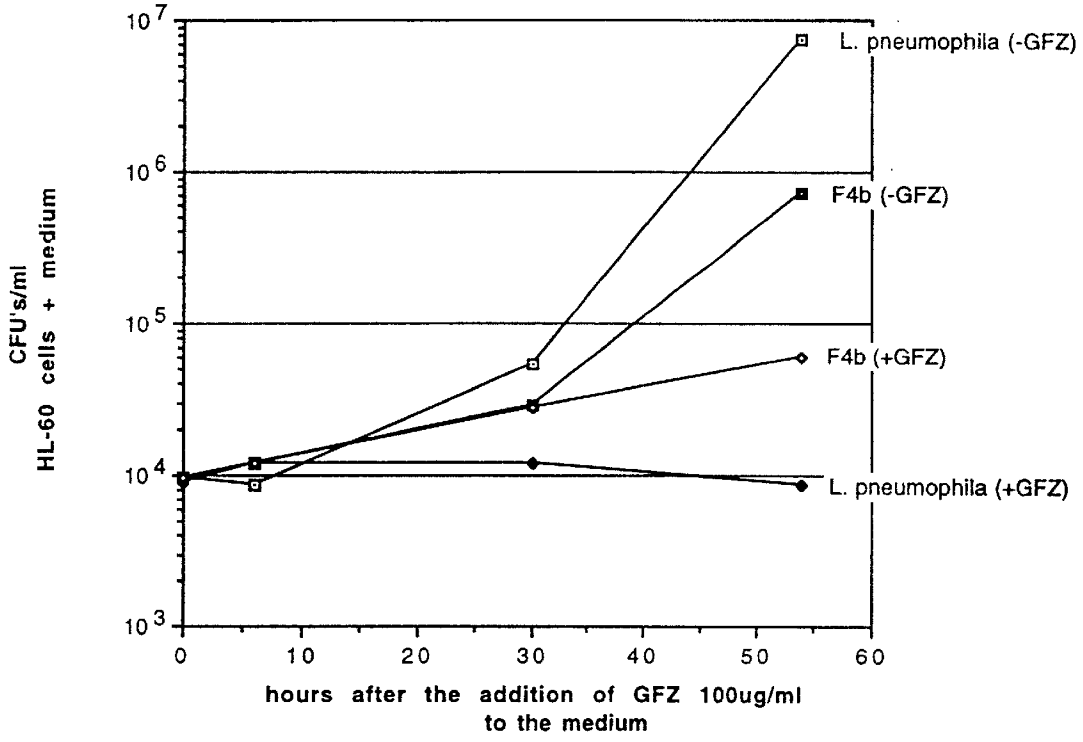
FIGS. 14A–14B. GFZ inhibits intracellar multiplication of *L. pneumophila* in PMA-differentiated HL-60 cells. (A) Monolayers of PMA-differentiated HL-60 cells were infected for 2.5 hours with *L. pneumophila* or F4b in the wells of 96 well microtiter plates. The wells were washed to remove extracellular bacteria, and medium containing 100 μg/ml of GFZ was added to the monolayers. Bacteria were titered at different time points by lysing the monolayers and counting the total number of CFU's present in the lysate and medium. (B) Monolayers of PMA-differentiated HL-60 cells were infected with increasing concentrations of *L. pneumophila* in the wells of 96 well microtiter plates. After 2.5 hours GFZ was added to the wells to a final concentration of 100 μg/ml. An MTT assay was performed after a five day incubation at 37° C. to assess HL-60 cell viability, Reduction of MTT by viable HL-60 cells was measured spectrophotometrically at 590 nm.
Figure 14B:
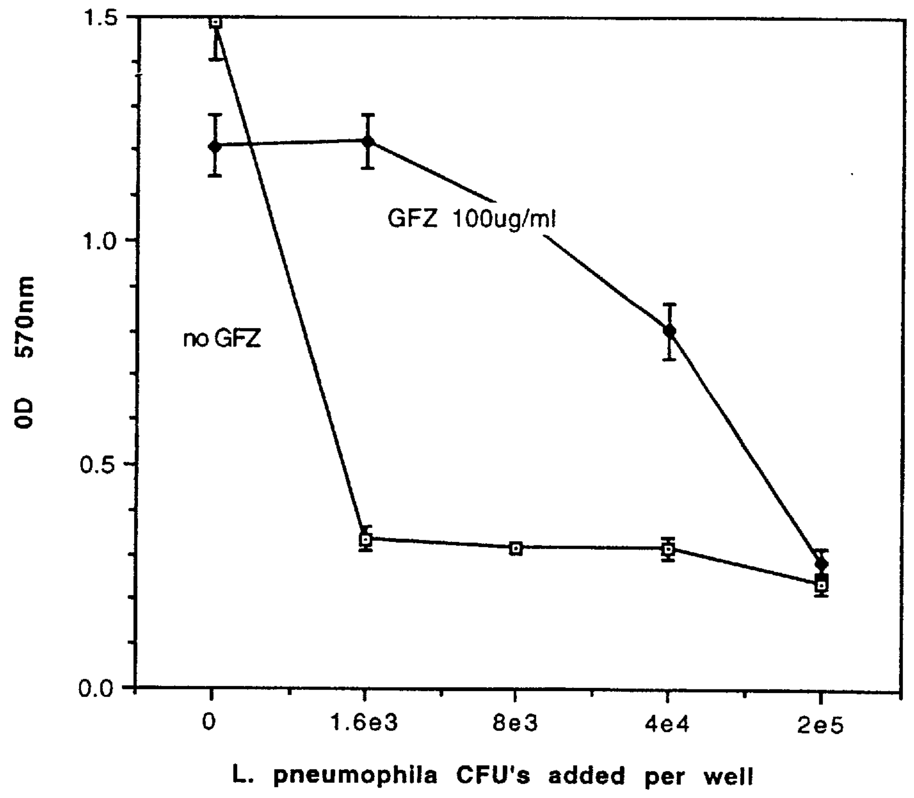

In HL-60 cells, *L. pneumophila* growth was inhibited by three logs over a 54 hour time period when GFZ was present in the media at a concentration of 100 μg/ml (FIG. 14A). Growth of F4b, the semi-resistant mutant, was only inhibited by one log by this concentration of GFZ. GFZ inhibited intracellular growth of *L. pneumophila* and of F4b to about the same extent as extracellular growth in AYE medium. The ability of GFZ to protect HL-60 cells from intracellular *L. pneumophila*-induced lysis was assessed using an MTT assay (FIG. 14B). This assay, which measures cell viability as a function of the ability of the monolayer to reduce MTT, showed increased viability of *L. pneumophila* infected HL-60 cells, in the presence of GFZ 100 μg/ml, over a five day incubation period.

Figure 15A:
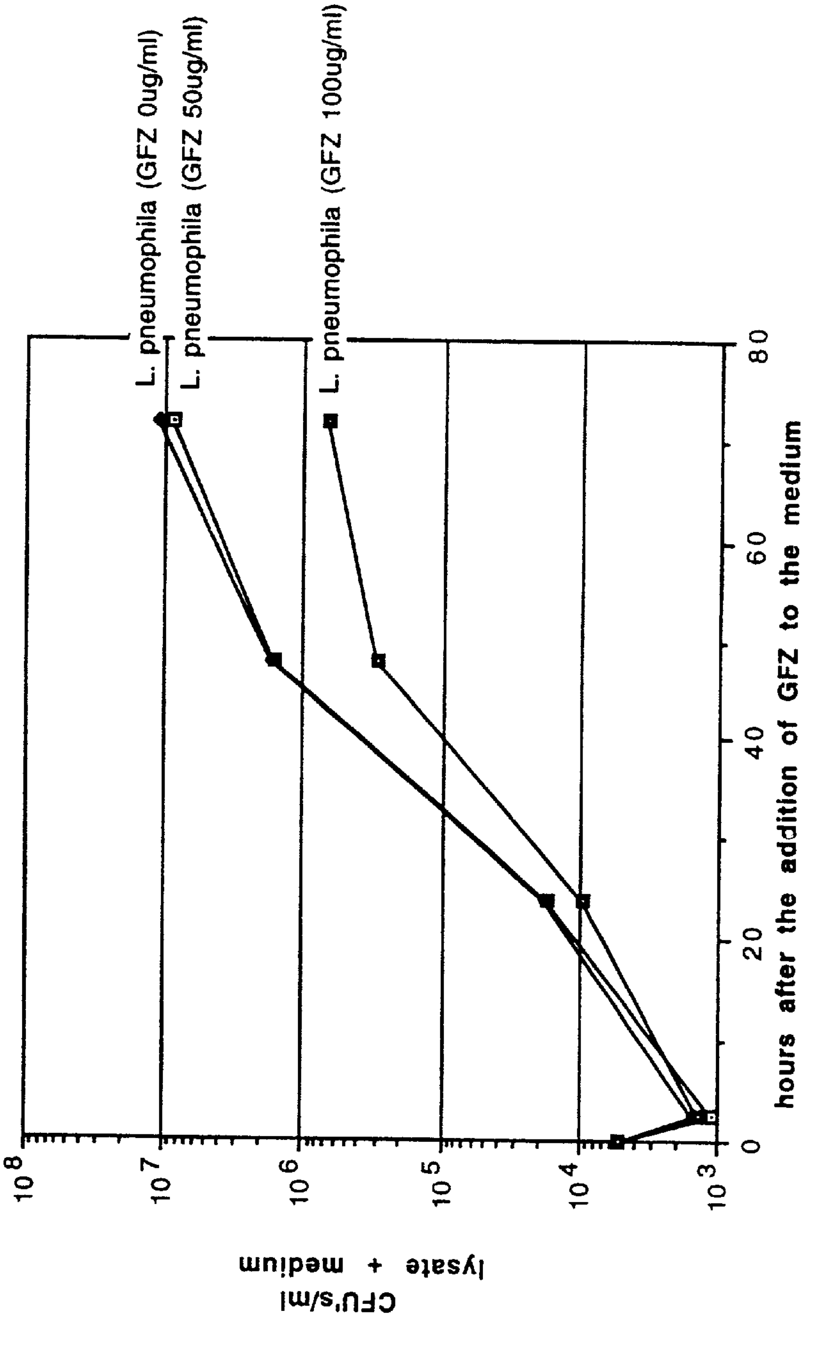
FIGS. 15A, 15B and 15C. GFZ inhibits intracellular multiplication of *L. pneumophila* in monocytic cells. (A) Monolayers of human peripheral blood derived monocytes were infected with *L. pneumophila* in the wells of 96 well microtiter plates. After 2.5 hours, the well were washed and medium containing GFZ 100 μg/ml was added to the monolayers. Bacteria were titered at different time points by lysing the monolayers and counting the total number of CFU's present in the lystate and medium of each well. (B) Monolayers of human peripheral blood derived macrophages were infected with F4b and titered for CFU's as described above. (C) Monolayers of the murine macrophage J774 cell line were infected with *L. pneumophila* and titered for CFU's as described above.
Figure 15B:
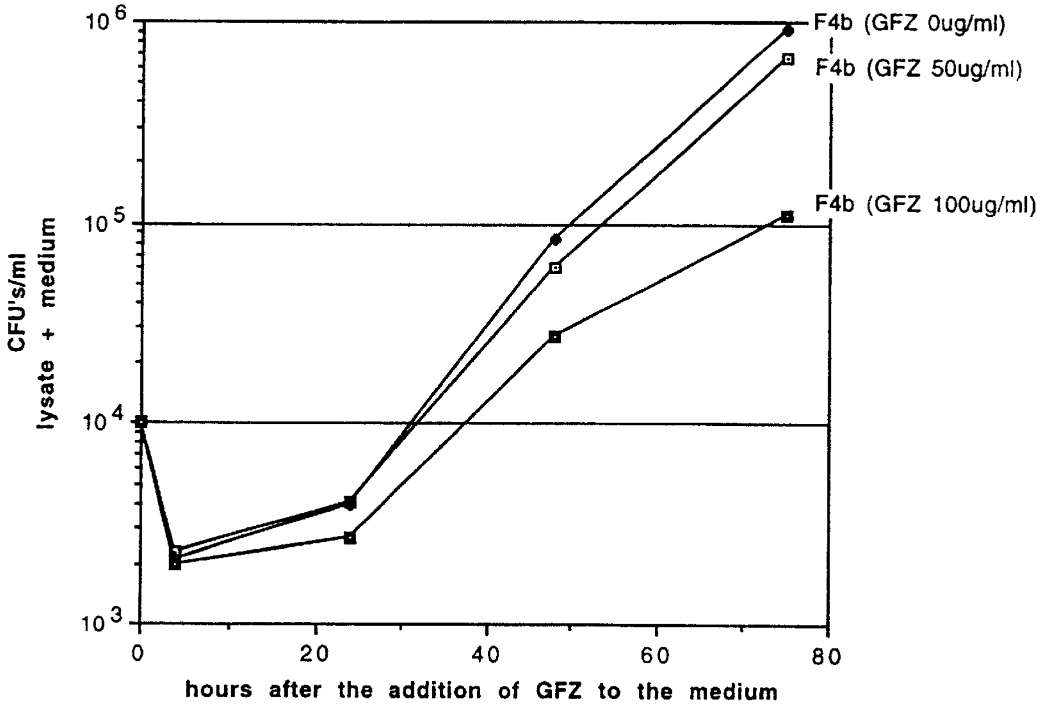
Figure 15C:
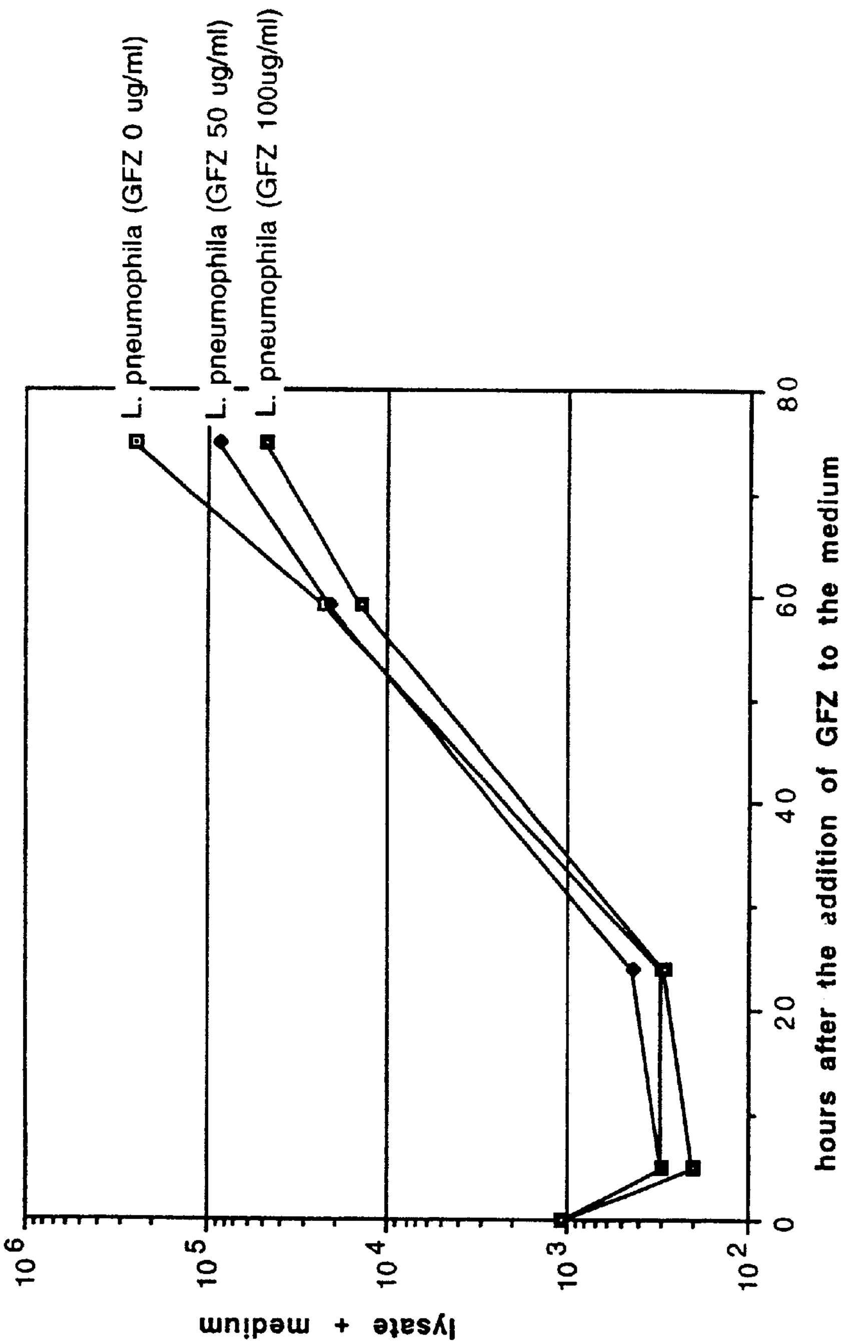

Growth of intracellular *L. pneumophila* in human monocytes was inhibited by GFZ(100 μg/ml) by one log after a 72 hour incubation period (FIG. 15A). Similarly, growth of F4b in human macrophages (FIG. 15B), and of *L. pneumophila* in mouse J774 macrophages (FIG. 15C) was inhibited by one log in the presence of GFZ 100 μg/ml. These experiments demonstrate that intracellular *L. pneumophila* remain sensitive to growth inhibition by GFZ.

A *L. pneumophila* 2.1 kb DNA Insert Complements an *E. coli* ts envM Mutant and Confers Sensitivity to GFZ Based on the above arguments, it is possible to hypothesize that GFZ affects the inhA homologous gene in *L. pneumophila*. Since InhA from *M. tuberculosis* has significant sequence similarity (40% identity over 203 amino acids) to the EnvM protein of *E. coli*, a cloning strategy was employed in which a temperature sensitive envM *E. coli* mutant, ts100, was transformed with DNA from a *L. pneumophila* library. A 2.1 kb insert of *L. pneumophila* DNA, expressed from a pBluescript vector, was found to complement the EnvM ts phenotype. When the envM ts mutant was grown at the permissive temperature (30° C.), with or without the insert, it was not sensitive to GFZ. However, when the ts envM *E. coli* was grown at the restrictive temperature (420C) on low osmolarity LB plates, the ts EnvM enzyme was nonfunctional, and growth was dependent on the expression of the homologous *L. pneumophila* enzyme encoded by the 2.1 kb DNA insert. Under restrictive conditions (42° C. on low osmolarity LB plates), the ts envM *E. coli* strain was sensitive to GFZ indicating that the protein encoded by the 20.1 kb DNA is the target, or a target, of GFZ (FIG. 16).

Disks containing 5 mg GFZ were required to affect growth of ts100envM:pBsk2.1 at 42° C. Whether this indicates differences in the substrates and products of EnvM in *E. coli* and *L. pneumophila* is uncertain. For example, if GFZ predominantly interferes with the ability of the *L. pneumophila* enzyme to utilize branched-chain or long chain fatty acid precursors, but does not interfere with the ability of the enzyme to utilize straight chain or short chain precursors, then GFZ would be expected to have less of an effect in *E. coli* which synthesizes most, if not all, of its fatty acids from B-hydroxy butyrate, a four carbon precursor of straight chain fatty acid synthesis. It has been recently demonstrated that the *E. coli* EnvM enzyme reduces a four carbon fatty acid crotonyl CoA substrate, while the homologous *M. tuberculosis* InhA enzyme will not reduce fatty acid substrates less than eight carbons long. Although untested, the homologous enzymes in *E. coli* and *M. tuberculosis* may differ significantly in their ability to accept and reduce branched chain fatty acid precursors.

Since the 20.1 kb *L. pneumophila* insert confers GFZ sensitivity, the next step would be to sequence the envM homologous gene contained in this insert. Once the gene is sequenced it can be tagged and expressed from high copy plasmids to facilitate purification for biochemical assays. Such assays may be used to directly assess in vitro inhibition of enzyme function by GFZ. EnvM and InhA activity have been measured in vitro by a NADH oxidation assay. In this assay, the purified enzyme, fatty acid CoA substrate, and NADH are combined in a cuvette, and NADH oxidation is measured over time at 340 nm in a spectrophotometer. This assay may be utilized to test the purified EnvM homologous enzyme. GFZ may inhibit NADH oxidation.

Once the *L. pneumophila* envM homologous gene is sequenced, PCR can be used to pull out the homologous gene from the GFZ semi-resistant mutant F4b. This gene can then be transformed into wild type *L. pnuemophila* to see if its expression confers resistance to GFZ. Additionally the homologous protein from GFZ semi-resistant F4b can be tested for resistance to GFZ biochemically.

It is possible that there is more that one enoyl reductase in *L. pneumophila* (*E. coli* contains two known enoyl reductases). The envM homologous gene can also be used to hybridize to other potential enoyl reductases in a *L. pneumophila* library, and potentially pull out other GFZ sensitive targets. Once the target genes are identified, site-directed mutagenesis can be used to identify the GFZ and substrate binding sites.

Discussion

In summary, a compound, GFZ, was identified which appears to inhibit fatty acid synthesis in several species of bacteria containing branched chain fatty acids. The GFZ target in *L. pneumophila* may be fully characterized and utilizing both genetic and biochemical approaches. Once the target has been identified, site-directed mutagenesis can be used for structure-function analysis to determine its GFZ binding site. Although the enzymatic target is found in other organisms beyond Mycobacteria, this enzyme has not been utilized as a target in any other species of bacteria. GFZ appears to have a novel and essential target site on the enzyme, since cross-resistance associated with other antibiotics has not been seen, and no high level resistant mutants have been obtained. It is possible that bacteria that do not contain branched chain fatty acids have a similar enzymatic site that can be targeted by other compounds or GFZ derivatives. Sensitivity can be tested biochemically using the NADH oxidation assay described above. Identification of the protein targeted by gemfibrozil, and the role of this protein in synthesizing fatty acids from specific precursors, and which enzymatic sites are important for these reactions, should be informative for both basic biology and for medicinal therapy. The ability of GFZ to inhibit synthesis of some, but not all fatty acid precursors in bacteria suggests it may have a similar effect in eukaryotic cells. Thus, these studies may provide insight into the mechanism by which this drug lowers blood lipids in humans.

REFERENCES

Brown, W. V. Potential use of fenofibrate and other fibric acid derivatives in the climic. *Am. J. Med.,* 1987, 83, Suppl. 5B, 85–89.

Oliver, M. F.; Heady, J. A.; Morris, J. N. and Cooper, M. M. A co-operative trial in the primary prevention of ischaemic heart disease using clofibrate. *Br. Heart J.,* 1987, 40, 1069–1118.

Palmer, R. H. Prevalence of gallstones in hyperlipidemia and incidence during treatment with clofibrate and/or cholestyramine. *Trans. Assoc. Am. Physicians,* 1987, 91, 424–432.

What is claimed is:

1. A method of inhibiting activity of enoyl reductase enzyme in a cell which comprises contacting the cell with a compound consisting of the structure set forth below, or a pharmaceutically acceptable salt or ester thereof, which compound is in an amount effective to inhibit the activity of the enzyme:

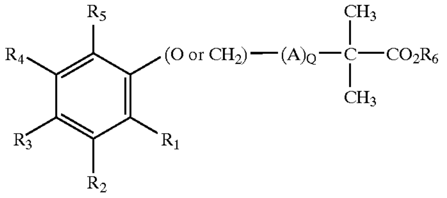

wherein each of $R_1$, $R_2$, $R_3$, $R_4$, $R_5$ and $R_6$ is independently selected from the group consisting of H, F, Cl, Br, I, —OH, —$OR_7$, —CN, —$COR_7$, —$SR_7$, —$N(R_7)_2$, —$NR_7COR_8$, —$NO_2$, —$(CH_2)_pOR_7$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, and heteroaryl;

wherein each of $R_7$ and $R_8$ is independently selected from the group consisting of H, F, Cl, Br, I, —OH, —CN, —COH, —$SH_2$, —$NH_2$, —NHCOH, —$(CH_2)_pOH$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, and heteroaryl;

wherein A is selected from the group consisting of —$N_2$—, —NH—, —CH═C═CH—, —C≡C—CHOH—, —C≡C—$CH_2$—, —$CH_2$—$CH_2$—O—, —$CH_2$—$CH_2$—$CH_2$—O—, —S—, —S(═O)$_2$—, —C(═O)—, —C(═O)—O—, —NH—C(═O)—, and —C (═O)—NH—; and wherein each of Q and p are independently an integer from 1 to 10, and if Q is 1, A is selected from the group consisting of a ($C_1$–$C_{10}$)-alkyl chain, a ($C_2$–$C_{10}$)-alkenyl chain, a ($C_2$–$C_{10}$)-alkylene chain or a ($C_2$–$C_{10}$)-alkynyl chain which is branched or unbranched, substituted or unsubstituted and is optionally interrupted 1 to 3 times by —O— or —S— or —N—.

2. The method of claim 1, wherein $R_1$=$R_4$=$CH_3$ or —OH, $R_2$=$R_3$=$R_5$=$R_6$=H or —OH,

A=$CH_2$ and Q=1.

3. The method of claim 1, wherein $R_3$=Cl, $R_1$=$R_2$=$R_4$=$R_5$=$R_6$=H or —OH, and Q=1.

4. The method of claim 1, wherein $R_3$ =

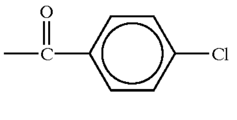

$R_6$=$CH(CH_3)_2$, $R_1$=$R_2$=$R_4$=$R_5$=H or —OH, and Q=1.

5. The method of claim 1, wherein $R_3$=Cl $R_6$=$C_2H_5$, $R_1$=$_2$=$R_4$=$R_5$=H or —OH, and Q=1.

6. The method of claim 1, wherein the enzyme is in a bacterium.

7. The method of claim 6, wherein bacterium is *Legionella pneumophila, Mycobacterium tuberculosis, Bacillus subtilis, Bacillus Mecraterium, Pseudomonas Oleovorans, Alcalicrenes eutrophus*, Rhodococcus species, *Citrobacter freundi*, Group A Streptococcus species, Coag neg *Staphylococcus aureus* or Nocardia species.

8. The method of claim 1, wherein the enzyme is in a cell.

9. The method of claim 8, wherein the cell is a mammalian cell.

10. The method of claim 1, wherein the concentration of the compound is from about 5 μg/ml to about 100 μg/ml.

11. The method of claim 1, wherein the concentration of the compound is 20 μg/ml.

12. A method of selecting a compound which inhibits the enzymatic activity of enoyl reductase which comprises:

(A) contacting enoyl reductase with the compound;

(B) measuring the enzymatic activity of the enoyl reductase of step (A) compared with the enzymatic activity of enoyl reductase in the absence of the compound, and selecting the compound which inhibits the enzymatic activity of enoyl reductase wherein the compound has the structure:

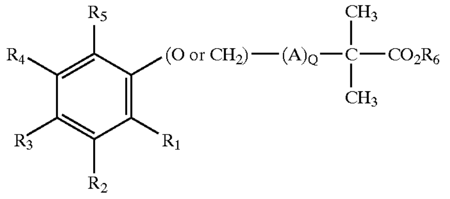

wherein each of $R_1$, $R_2$, $R_3$, $R_4$, $R_5$ and $R_6$ is independently selected from the group consisting of H, F, Cl, Br, I, _OH, —$OR_7$, —ON, —$COR_7$, —$SR_7$—, —$N(R_7)_2$, —$NR_7COR_8$, —$NO_2$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, and heteroaryl;

wherein each of $R_7$ and $R_8$ is independently selected from the group consisting of H, F, Cl, Br, I, —OH, —CN, —COH, —$SH_2$, —$NH_2$, —NHCOH, —$(CH_2)_p$OH, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, and heteroaryl;

wherein A is selected from the group consisting of —$N_2$—, —NH—, —CH=C=CH—, —C≡C—CHOH—, —C≡C—$CH_2$—, —$CH_2$—$CH_2$—O—, —$CH_2$—$CH_2$—$CH_2$—O—, —S—, —S(=O)$_2$, —C(=O)—, —C (=O)—O—, —NH—C(=O)—, and —C (=O)—NH—; and wherein each of Q and p is independently an integer from 1 to 10, and if Q is 1, A is selected from the group consisting of a ($C_1$–$C_{10}$)-alkyl chain, a ($C_2$–$C_{10}$)-alkenyl chain, a ($C_2$–$C_{10}$)-alkylene chain or a ($C_2$–$C_{10}$)-alkynyl chain which is branched or unbranched, substituted or unsubstituted and is optionally interrupted 1 to 3 times by —O— or —S— or —N—.

13. The method of claim 1, wherein A is selected from the group consisting of ($C_2$–$C_{10}$)-alkylene chain, ($C_1$–$C_{10}$)-alkyl chain, ($C_2$–$C_{10}$)-alkenyl chain or ($C_2$–$C_{10}$)-alkynyl chain which is branched or unbranched, substituted or unsubstituted and is optionally interrupted 1 to 3 times by —O— or —S— or —N—.

14. The method of claim 12 wherein the compound contacts enoyl reductase at the site at which gemfibrozil contacts the reductase.

15. The method of claim 11 wherein the compound is gemfibrozil.

16. The method of claim 12, wherein $R_6$ is selected from the group consisting of H, F, Cl, Br, I, —OH, and —$NO_2$.

17. The method of claim 1, wherein $R_6$ is selected from the group consisting of H, F, Cl, Br, I, —OH, and —$NO_2$.

* * * * *